(12) United States Patent
Estes

(10) Patent No.: US 10,661,007 B2
(45) Date of Patent: May 26, 2020

(54) OPERATING AN INFUSION PUMP SYSTEM

(71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 174 days.

(21) Appl. No.: 15/240,220

(22) Filed: Aug. 18, 2016

(65) Prior Publication Data
US 2017/0043084 A1 Feb. 16, 2017

Related U.S. Application Data

(62) Division of application No. 13/782,468, filed on Mar. 1, 2013, now Pat. No. 9,446,186.

(51) Int. Cl.
| A61M 5/142 | (2006.01) |
| A61M 5/14 | (2006.01) |
| A61M 5/145 | (2006.01) |
| A61M 5/315 | (2006.01) |

(52) U.S. Cl.
CPC ....... *A61M 5/14244* (2013.01); *A61M 5/1413* (2013.01); *A61M 5/14248* (2013.01); *A61M 5/14566* (2013.01); *A61M 2005/14268* (2013.01); *A61M 2005/31518* (2013.01); *A61M 2205/13* (2013.01); *A61M 2205/18* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2230/201* (2013.01)

(58) Field of Classification Search
CPC .... A61M 2205/18; A61M 2005/14208; A61M 2205/52; A61M 2230/005
See application file for complete search history.

(56) References Cited

U.S. PATENT DOCUMENTS

| 6,126,595 A | 10/2000 | Amano |
| 6,233,471 B1 | 5/2001 | Berner et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |

(Continued)

FOREIGN PATENT DOCUMENTS

| CA | 2543545 | 5/2005 |
| DE | 196 27 619 | 1/1998 |

(Continued)

OTHER PUBLICATIONS

Asante Pearl, Insulin Pump User Manual, 2012 (180 pages).

(Continued)

*Primary Examiner* — Emily L Schmidt
(74) *Attorney, Agent, or Firm* — Fish & Richardson P.C.

(57) ABSTRACT

Some embodiments of an infusion pump system can be configured to provide improved safety monitoring features so that a user receives proper dosage amounts.

15 Claims, 14 Drawing Sheets

(56) References Cited

U.S. PATENT DOCUMENTS

| | | |
|---|---|---|
| 6,544,229 B1 | 4/2003 | Danby et al. |
| 6,547,764 B2 | 4/2003 | Larsen et al. |
| 6,551,276 B1 | 4/2003 | Maim et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Maim |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0016534 A1 | 2/2002 | Trepagnier et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0049179 A1* | 3/2005 | Davidson ............... G16H 20/10 703/11 |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |

(56) References Cited

U.S. PATENT DOCUMENTS

| | | |
|---|---|---|
| 2006/0206054 A1 | 9/2006 | Shekalim |
| 2006/0247581 A1 | 11/2006 | Pedersen et al. |
| 2007/0073228 A1 | 3/2007 | Memoe et al. |
| 2007/0073235 A1 | 3/2007 | Estes et al. |
| 2007/0073236 A1 | 3/2007 | Mernoe et al. |
| 2007/0100222 A1* | 5/2007 | Mastrototaro ........... A61B 5/01 600/365 |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0125700 A1 | 5/2008 | Moberg et al. |
| 2008/0172027 A1 | 7/2008 | Blomquist |
| 2008/0306444 A1 | 12/2008 | Brister |
| 2008/0312512 A1 | 12/2008 | Brukalo |
| 2009/0069787 A1 | 3/2009 | Estes et al. |
| 2009/0275887 A1* | 11/2009 | Estes ................. A61M 5/14244 604/67 |
| 2010/0121170 A1* | 5/2010 | Rule .................... A61B 5/1427 600/365 |
| 2010/0185142 A1* | 7/2010 | Kamen ............. A61M 5/14224 604/66 |
| 2011/0098637 A1 | 4/2011 | Hill |
| 2011/0098674 A1* | 4/2011 | Vicente ............. A61M 5/14244 604/504 |
| 2011/0224523 A1* | 9/2011 | Budiman ........... A61B 5/14532 600/365 |
| 2012/0065894 A1 | 3/2012 | Tubb et al. |
| 2012/0172802 A1 | 7/2012 | Blomquist |
| 2013/0053818 A1 | 2/2013 | Estes et al. |
| 2013/0053820 A1 | 2/2013 | Estes et al. |
| 2013/0116649 A1 | 5/2013 | Breton et al. |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 1990/015928 | 12/1990 |
| WO | WO 1997/021457 | 6/1997 |
| WO | WO 1998/011927 | 3/1998 |
| WO | WO 1998/057683 | 12/1998 |
| WO | WO 1999/021596 | 5/1999 |
| WO | WO 1999/039118 | 8/1999 |
| WO | WO 1999/048546 | 9/1999 |
| WO | WO 2001/072360 | 10/2001 |
| WO | WO 2001/091822 | 12/2001 |
| WO | WO 2001/091833 | 12/2001 |
| WO | WO 2002/040083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |
| WO | WO 2008/016621 | 2/2008 |

OTHER PUBLICATIONS

Collins and Lee, "Microfluidic flow transducer based on the measurement of electrical admittance," *Lab Chip*, 2003, 12 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

International Search Report and Written Opinion in International Application No. PCT/US2014/19441, dated Aug. 5, 2014, 18 pages.

Medtronic News Release, "Medtronic Receives FDA Approval for World's First Insulin Pump with Real-time Continuous Glucose Monitoring," Apr. 13, 2006, 3 pages.

Patent Abstracts of Japan, vol. 1999, No. 04, and JP 11 010036, Apr. 30, 1999 and Jan. 19, 1999, Toray Ind. Inc.

Walsh et al., "Guidelines for Insulin Dosing in Continuous Subcutaneious Insulin Infusion Using New Formulas from a Retrospective Study of Individuals with Optimal Glucose Levels", J. Diabetes Science and Technology, vol. 4 Issue 5, Sep. 2010 (8 pages).

Walsh et al.,"Guidelines for Optimal Bolus Calculator Settings in Adults", J. Diabetes Science and Technology; vol. 5 Issue 1; Jan. 2011 (7 pages).

Supplemental European Search Report in Application No. 14756333.2, dated Oct. 6, 2016, 4 pages.

* cited by examiner

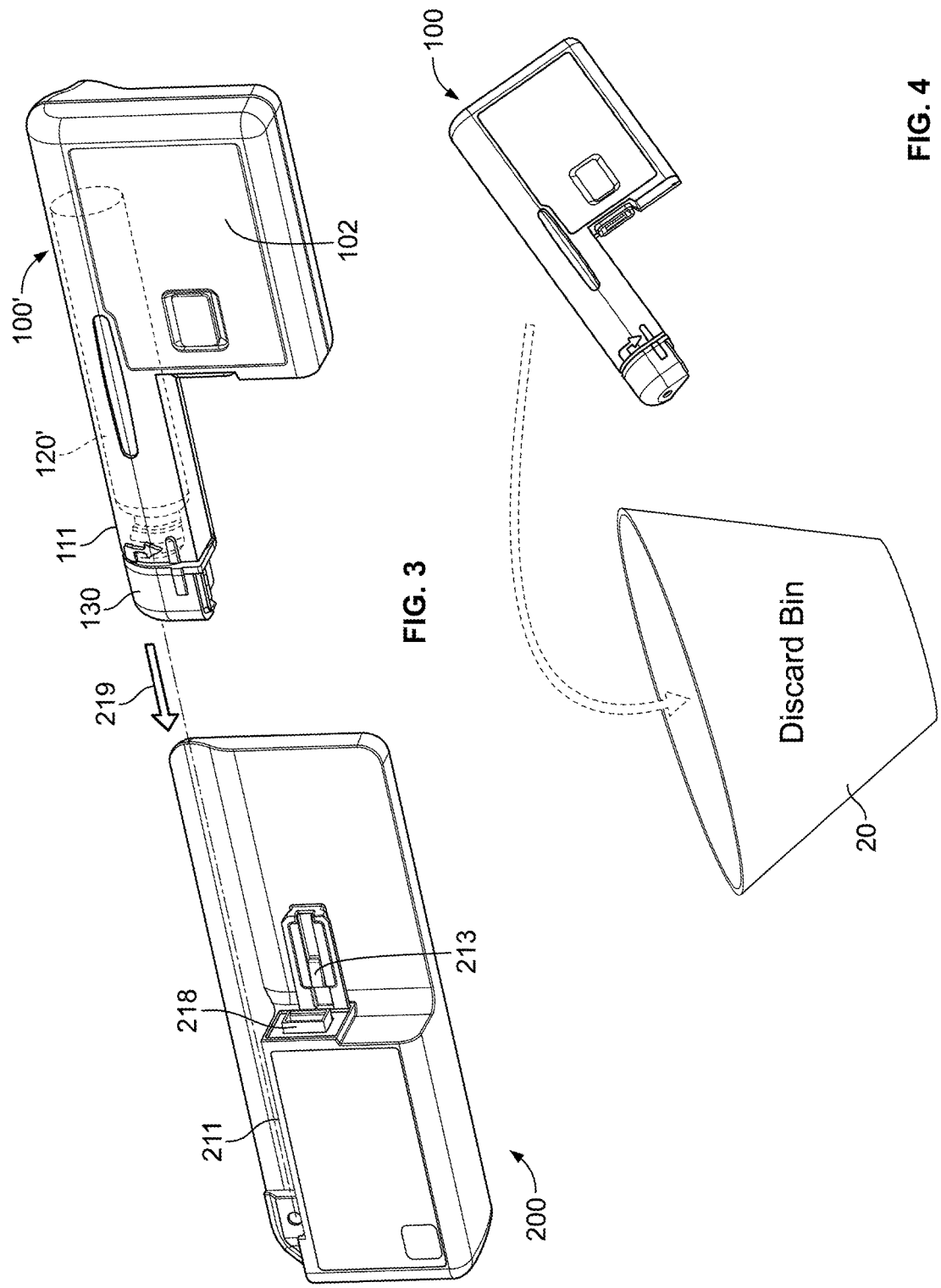

OPERATING AN INFUSION PUMP SYSTEM

CROSS-REFERENCE TO RELATED APPLICATION

This application is a division of U.S. application Ser. No. 13/782,468, filed Mar. 1, 2013, the entire contents of which are hereby incorporated by reference.

TECHNICAL FIELD

This document relates to an infusion pump system, such as a portable infusion pump system for dispensing insulin or another medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often need to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

In some circumstances, an infusion pump device can store (via input from a clinician or a user) a number of user-specific settings that are customized for the particular user. In one example, an infusion pump device can be programmed to store a user's insulin sensitivity (e.g., in units of mg/dL/insulin unit), which can be employed by the infusion pump system when calculating correction bolus dosage for that particular user. In another example, an infusion pump device can be programmed to store a user's carbohydrate ratio (e.g., in units of g/insulin unit), which can be employed by the infusion pump system when calculating meal bolus dosage for that particular user. In many cases, these user-specific settings are manually input into the infusion pump device via a user interface buttons on the infusion pump device. If any of these user-specific settings are erroneously input into the infusion pump system (e.g., due to a transcribing error or other error when manually inputting the data), the resulting consequences could lead to improper bolus dosage calculations, blood glucose levels that are unnecessarily too high or too low.

Furthermore, even if the user-specific settings are correctly input and stored by the infusion pump device, other types of errors can result in the user receiving an improper dosage of the insulin or other medicine. For example, if an infusion set cannula is connected to the infusion pump device but is not properly seated at the user's skin, the infusion pump device may dispense a dosage of medicine that is wholly or partially not infused into the user's body.

SUMMARY

Some embodiments of an infusion pump system can be configured to provide improved safety monitoring features so that a user receives proper dosage amounts. In a first example, the infusion pump system can be configured to determine whether a newly input value for a first user-specific setting is out of balance with a different user-specific setting. If so, a user interface of the infusion pump system can alert the user and prompt the user to replace the possibly erroneous value for the first user-specific setting. In a second example, the infusion pump system can be configured to retrospectively evaluate previously stored values of user-specific settings and dosage history to determine if any of the values is out of balance with a different user-specific setting or dosage history value. If so, a user interface of the infusion pump system can alert the user and prompt the user to take corrective actions (e.g., provide a new value for a user-specific setting, provide a new dosage schedule, review troubleshooting instructions, or the like). In a third example, the infusion pump system can configured to monitor whether the dispensed medicine is being properly transferred from the infusion set tubing into the user's body. For instance, the infusion pump system can evaluate if user's blood glucose levels over a period of time after dispensation of a bolus dosage is decreasing (or, in some embodiments, the rate of change is decreasing) and if not, output an alert indicative of a possible problem with the infusion set device. In a fourth example, the infusion pump system can be configured to automatically calculate and implement a set of generally safe values for a number of different user-specific settings in response to user input of a value for one different user-specific setting.

Particular embodiments described herein include an insulin infusion pump system, which may include a portable housing defining a space to receive a supply of insulin and may also include a pump drive system to dispense insulin from the portable housing when the insulin is received in the space. The insulin infusion pump system may further include control circuitry that electrically communicates with the pump drive system to control dispensation of the insulin from the portable housing when the insulin is received in the space. Also, the insulin infusion pump system may include a user interface connected to the control circuitry and configured to receive user input of a value for a first user-specific setting. The control circuitry may be configured to output an alert via the user interface in response to user input of the value for the first user-specific setting that is outside of a predetermined range dependent at least partially upon a previously stored value for a second user-specific setting that is different from the first user-specific setting.

Some embodiments described herein include a medical infusion pump system, which may include a portable housing defining a space to receive a supply of medicine and may also include a pump drive system to dispense medicine from the portable housing when the medicine is received in the space. The medical infusion pump system may include control circuitry that electrically communicates with the pump drive system to control dispensation of the medicine from the portable housing when the medicine is received in the space. Optionally, the control circuitry may include one or more computer readable memory devices storing values for user-specific settings and pump usage parameters. The medical infusion pump system may also include a user interface connected to the control circuitry and having a display screen. The control circuitry may be configured to output an alert via the user interface in response a stored value for a first one of the user-specific settings and the pump usage parameters being outside of a predetermined range that is dependent at least partially upon a stored value for a second one of the user-specific settings and the pump usage parameters.

In various embodiments of an insulin infusion pump system described herein, the insulin infusion pump system may include a portable housing defining a space to receive a supply of insulin and may also include a pump drive system to dispense insulin from the portable housing when the insulin is received in the space. The insulin infusion pump system may further include control circuitry that electrically communicates with the pump drive system to control dispensation of the insulin from the portable housing when the insulin is received in the space. Optionally, the control circuitry may be configured to receive blood glucose information over a period of time. The insulin infusion pump system may also include a user interface connected to the control circuitry and having a display screen. The user interface may be configured to receive user input to initiate a bolus dosage of the insulin. The control circuitry may output an alert via the user interface in response to the control circuitry detecting an infusion set error based at least in part upon the blood glucose information received by the control circuitry over the period of time.

Some embodiments described herein include a method of operating a portable infusion pump system. The method may include dispensing medicine from a portable housing of an infusion pump system. The method may also include receiving user input at a user interface of the infusion pump system indicative of a value for a first user-specific setting. Optionally, the method may further include outputting an alert via the user interface of the infusion pump system in response to a determination by the infusion pump system that the user input of the value for the first user-specific setting that is outside of a predetermined range dependent at least partially upon a previously stored value for a second user-specific setting that is different from the first user-specific setting.

In particular embodiments, a method of operating a portable infusion pump may include dispensing medicine from a portable housing of an infusion pump system. The method may further include storing values for user-specific settings and pump usage parameters in one or more computer readable memory devices of control circuitry of the infusion pump system. Optionally, the method may also include outputting an alert via a user interface of the infusion pump system in response a stored value for a first one of the user-specific settings and the pump usage parameters being outside of a predetermined range that is dependent at least partially upon a stored value for a second one of the user-specific settings and the pump usage parameters.

In various embodiments described herein, a method of operating a portable infusion pump system may include dispensing medicine from a portable housing of an infusion pump system. The method may also include receiving user input at a user interface of the infusion pump system to initiate a bolus dosage of the medicine. The method may also include receiving at the infusion pump system blood glucose information indicative of a user's blood glucose measurements over a period of time. Optionally, the method may include outputting an alert via the user interface of the infusion pump system in response to the infusion pump system detecting an infusion set error based at least in part upon the blood glucose information received by the infusion pump system over the period of time.

In some embodiments described herein, an insulin infusion pump system may include a portable housing defining a space to receive a supply of insulin and may also include a pump drive system to dispense insulin from the portable housing when the insulin is received in the space. The insulin infusion pump system may include control circuitry that electrically communicates with the pump drive system to control dispensation of the insulin from the portable housing when the insulin is received in the space. Also, the insulin infusion pump system may include a user interface connected to the control circuitry and having a display screen. The user interface may be configured to receive user input for a value of a first user-specific setting. The control circuitry may generate values for a set of user-specific settings that are different from the first user-specific setting in response to the user input for the value of the first user-specific setting.

Some or all of the embodiments described herein can provide one or more of the following benefits. First, some embodiments of an infusion pump system can be equipped with a controller device that is configured to determine whether a newly input value for a first user-specific setting is out of balance with a different user-specific setting. In particular circumstances, the controller device can be configured to determine whether the newly input value for the user-specific setting is within a selected range of values selected based at least in part on the previously stored value for the different user-specific setting. For example, the controller device can be configured to compare any of the following user-specific settings: carbohydrate ratio, insulin sensitivity, scheduled basal dose per day, anticipated total bolus dose per day, and user weight. If the controller device for the infusion pump system determines that the newly input value for a particular user-specific setting is out of balance with the previously stored value for the different user-specific setting (e.g., not within the range of values calculated as a function of the previously stored value for the different user-specific setting), a user interface of the infusion pump system can output an alert the user. Optionally, the user interface may prompt the user either to "accept" newly input value even if it is out of balance with one or more other user-specific settings, or to "reject" the newly input value and thereafter provide a corrected value.

Second, particular embodiments of an infusion pump system can be equipped with a controller device that is configured to retrospectively evaluate previously stored values of user-specific settings and dosage history to determine if any of the values is out of balance with a different user-specific setting or dosage history value. For example, the controller device can be configured to store any of the following settings or historical measurements for use in the aforementioned retrospective analysis: carbohydrate ratio, insulin sensitivity, average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, frequency of using an auto-off alarm per day, and a frequency of cannula and tube primes per day. One or more of these aforementioned measurements can be analyzed by the controller device to determine whether there is a possible imbalance in a user-specific setting, a possible improper use of the pump system, or both. If so, a user interface of the infusion pump system can alert the user and prompt the user to take corrective actions (e.g., provide a new value for a user-specific setting, provide a new dosage schedule, review troubleshooting instructions, or the like).

Third, some embodiments of an infusion pump system can simultaneously provide a number of convenient options to the user when any of the aforementioned alerts is output by the system. For example, the infusion pump system may output an alert including a textual message on the user interface display screen in response to a detection that a user-specific setting is out of balance with one or more different user-specific setting, but the content of textual alert message can vary by the degree of imbalance or by the particular user-specific setting that is out of balance. Additionally, some embodiments of the infusion pump system can be configured to provide the user with an option to temporarily silence or disable the aforementioned alert for a period of time, after which the infusion pump system would again prompt the user review the user-specific settings and input a corrected value. The frequency of the alert output from the infusion pump system may vary by the degree of imbalance or by the particular user-specific setting that is out of balance. Furthermore, some embodiments of the infusion pump system can be configured to prevent the user from inputting a new value for a user-specific setting (e.g., by requiring the user to accept the previously stored value or to input a corrected value) that is not balance with one or more other user-specific setting within a predetermined tolerance level. In such circumstances, the level of imbalance tolerated can be adjustable, for example, in response to user input from a clinician or the user.

Fourth, particular embodiments of an infusion pump system can be configured to identify a potential problem with an infusion set (e.g., the insulin set cannula is not properly seated on the skin, or the like) based at least in part on an analysis of the user's blood glucose levels during a period of time after medicine is dispensed from the infusion pump reservoir. In one example, the infusion pump system can output an alert indicative of a possible problem with the infusion set device in response to a computational evaluation of the user's blood glucose levels over a predetermined period of time (e.g., about 15 minutes to about 75 minutes, preferably about 30 minutes to about 60 minutes) after dispensation of a bolus dosage. If the user's blood glucose levels is not decreasing (or, in some embodiments, the rate of change is not decreasing) during that predetermined time period, then the infusion pump system can output an alert indicative of a potential problem with the infusion set device and may furthermore prompt the user to check or replace the infusion set or otherwise provide troubleshooting instructions to the user.

Fifth, some embodiments of an infusion pump system can be configured to automatically generate a set of generally safe values for some user-specific settings in response to user input of a value for a particular, different user-specific settings. For example, the pump system can be configuration to provide an initial set-up procedure during which the pump system can prompt the user to input a value for a first user-specific setting. In response to receiving this piece of information, the pump system can then calculate (and automatically populate) suitable values for a set of various other user-specific settings. In doing so, the pump system can be configured to display the automatically generated values for review by the user, and to furthermore prompt the user to accept the automatically generated values for the user-specific settings.

Sixth, some embodiments of the infusion pump system are configured to be portable, wearable, and (in some circumstances) concealable. In such circumstances, a user may conveniently wear the infusion pump system on the user's skin under clothing or can carry the pump system in the user's pocket (or other portable location) while receiving the medicine dispensed from the pump reservoir.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3-4 are perspective views of the pump device of FIGS. 1-2 being discarded and the controller device of FIGS. 1-2 being reused with a new pump device.

Like reference symbols in the various drawings indicate like elements.

DETAILED DESCRIPTION OF ILLUSTRATIVE EMBODIMENTS

Figure 1:
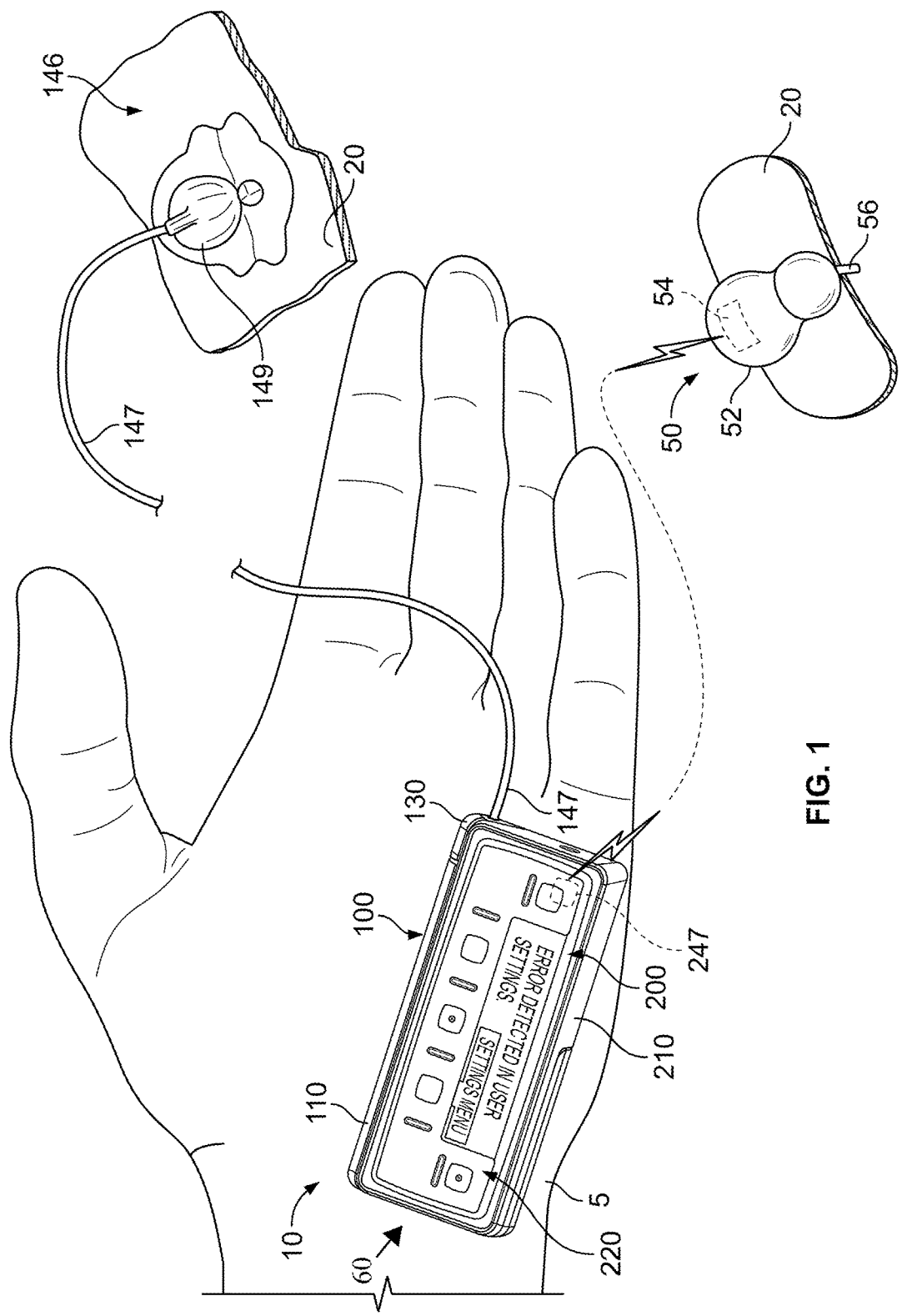
FIG. 1 is a perspective view of an infusion pump system, in accordance with some embodiments.

Referring to FIG. 1, some embodiments of an infusion pump system 10 can include a pump device 100 and a controller device 200. Optionally, the controller device can be configured to releasably attach with the pump device 100. The controller device 200 can electrically communicate with the pump device 100 to control a drive system housed in the pump device 100 to dispense a medicine to a user (e.g., through a tube 147 of an infusion set 146 in this example). When the controller device 200 and the pump device 100 are assembled together, the user can (in some embodiments)

conveniently wear the infusion pump system 10 on the user's skin under clothing, in a pouch clipped at the waist, or in the user's pocket while receiving the fluid dispensed from the pump device 100.

Briefly, in use, the pump device 100 in this embodiment is configured to removably attach to the controller device 200 in a manner that provides a secure fitting, an overall compact size, and a reliable electrical connection. For example, as described in more detail below in connection with FIGS. 2-4, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable. The controller device 200 can receive user input for purposes of storing a number of user-specific settings, which can subsequently employ some or all of the user-specific settings to provide user-specific dosage calculations or the like. In some embodiments, as described further below in connection with FIGS. 7A-10, the pump system 10 can be configured to perform a proactive or retroactive safety check of the one or more user-specific settings stored by the controller (e.g., to verify a safe balance with other settings, scheduled dosage amounts, or historical dosage amounts of the user).

Still referring to FIG. 1, in some embodiments, a glucose monitoring device 50 can be in communication with the infusion pump system 10 for the purpose of supplying data indicative of a user's blood glucose level to the controller device 200 included in the pump system 200. The infusion pump system 10 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit. In some embodiments, as described further below in connection with FIGS. 12A-13, the user's blood glucose data can be evaluated by the controller device 200 to detect possible problems with the infusion set 146.

The glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to a corresponding wireless communication device 247 housed in the pump system 10. In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to the communication device 247 arranged in the pump system 10). Alternatively, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some alternative embodiments, the monitoring device 50 can be in communication with the pump system 10 via a wired connection. In other embodiments of the pump system 10, test strips (e.g., blood test strips) containing a sample of the user's blood can be inserted into a strip reader portion of the pump system to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the pump system. In still other embodiments, characteristics of the user's blood glucose information can be entered directly into the pump system 10 via a user interface on the controller device 200.

Figure 2:
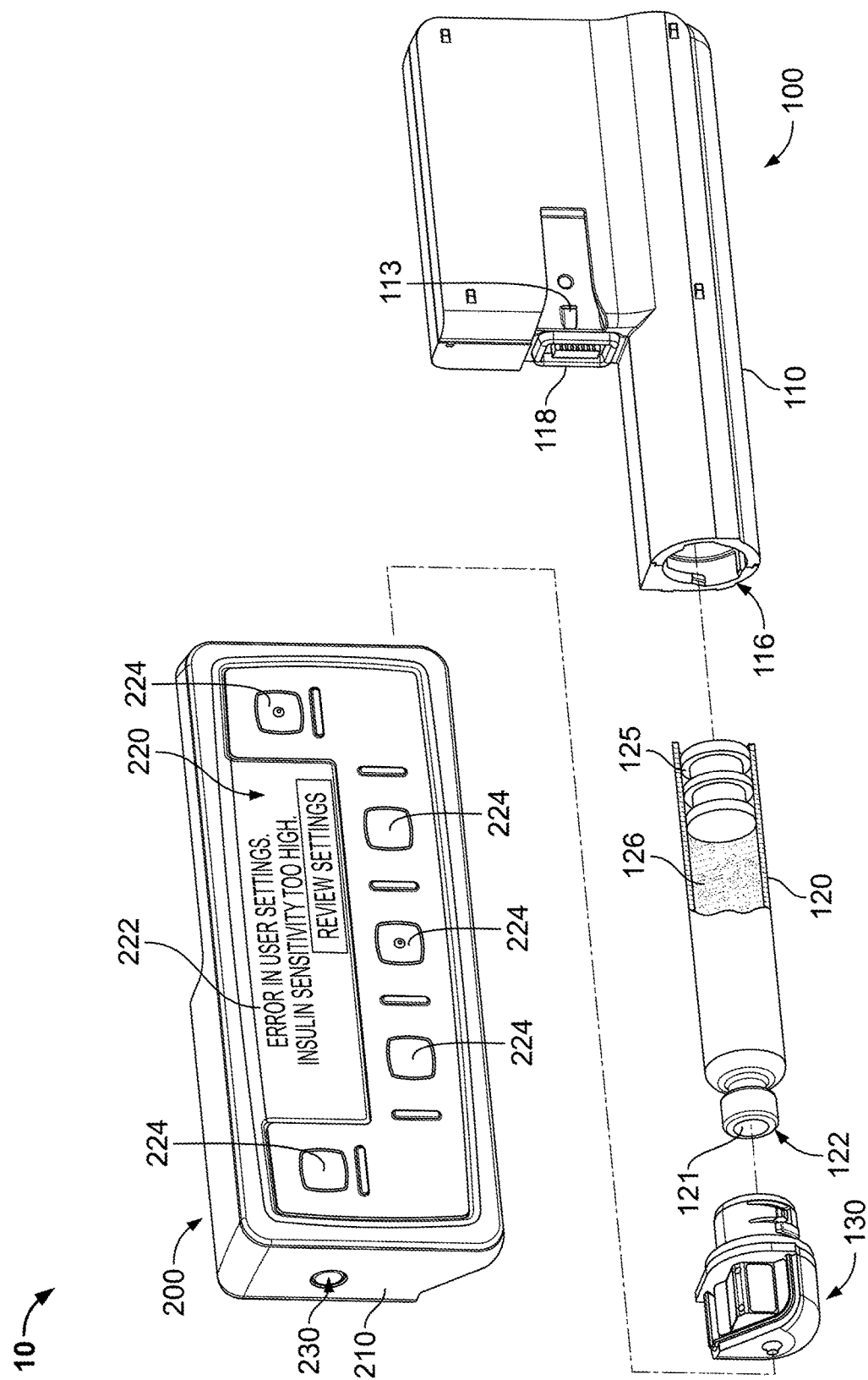
FIG. 2 is an exploded perspective view of an infusion pump system in accordance with some embodiments.

Referring now to FIG. 2, the pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (refer to FIG. 6) that advances a plunger 125 in the fluid cartridge 120 so as to dispense fluid therefrom. In this embodiment, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 3-4, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

The pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 2) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 2, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of the drive system (FIG. 6) of the pump device 100. As described in more detail below, the pump device 100 can include a drive system that causes controlled dispensation of the medicine or other fluid from the cartridge 120. In some embodiments, the drive system incrementally advances a piston rod (FIG. 6) longitudinally into the cartridge 120 so that the fluid is forced out of an output end 122. A septum 121 (FIG. 2) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 5) of the controller device 200 and from the power source 310 (refer to FIG. 6) of the pump device 100 may also be passed between the controller device 200 and the pump device 100.

As shown in FIG. 2, the pump device 100 can include an electrical connector 118 (e.g., having conductive pads, pins, and the like) that is exposed to the controller device 200 and that mates with a complementary electrical connector (refer to connector 218 in FIG. 3) on the adjacent face of the controller device 200. The electrical connectors 118 and 218 provide the electrical communication between the control circuitry (refer, for example, to FIG. 5) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 2, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIGS. 1-2). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas. The inspection light device 230 can also be used to notify the user to an alert condition of the pump system 10. For example, as described in more detail below, the inspection light device 230 can be activated when the controller has detected a possible problem with the infusion set 146. An activation of the inspection light device 230 can thereby provide a visual notification (as an alternative to, or in addition to, the visual notification provided on the display device 222) to the user that attention to the pump system 10 is warranted.

As shown in FIGS. 1-2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 3) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. Also, the pump device can include an adjustable latch 113 (FIG. 2) that is configured to releasably mate with a corresponding catch 213 (FIG. 3) of the controller device 200. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

The infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 depicted in FIG. 1 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 2) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 3) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 3-4, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with a subsequent new pump devices 100' and a new medicine cartridges 120' (FIG. 3). As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

As shown in FIGS. 3-4, the same controller device 200 can be reused with the new pump device 100' having the new medicine cartridge 120' retained therein, and the previously used pump device 100, including the exhausted medicine cartridge, can be discarded in a discard bin 20. The new pump device 100' (FIG. 3) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 of the new pump device 100' to the pump housing to retain the new medicine cartridge 120' therein (refer, for example, to FIG. 1). Although the tubing 147 of the infusion set 146 is not shown in FIG. 3, it should be understood that a new infusion set tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 3, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 5:
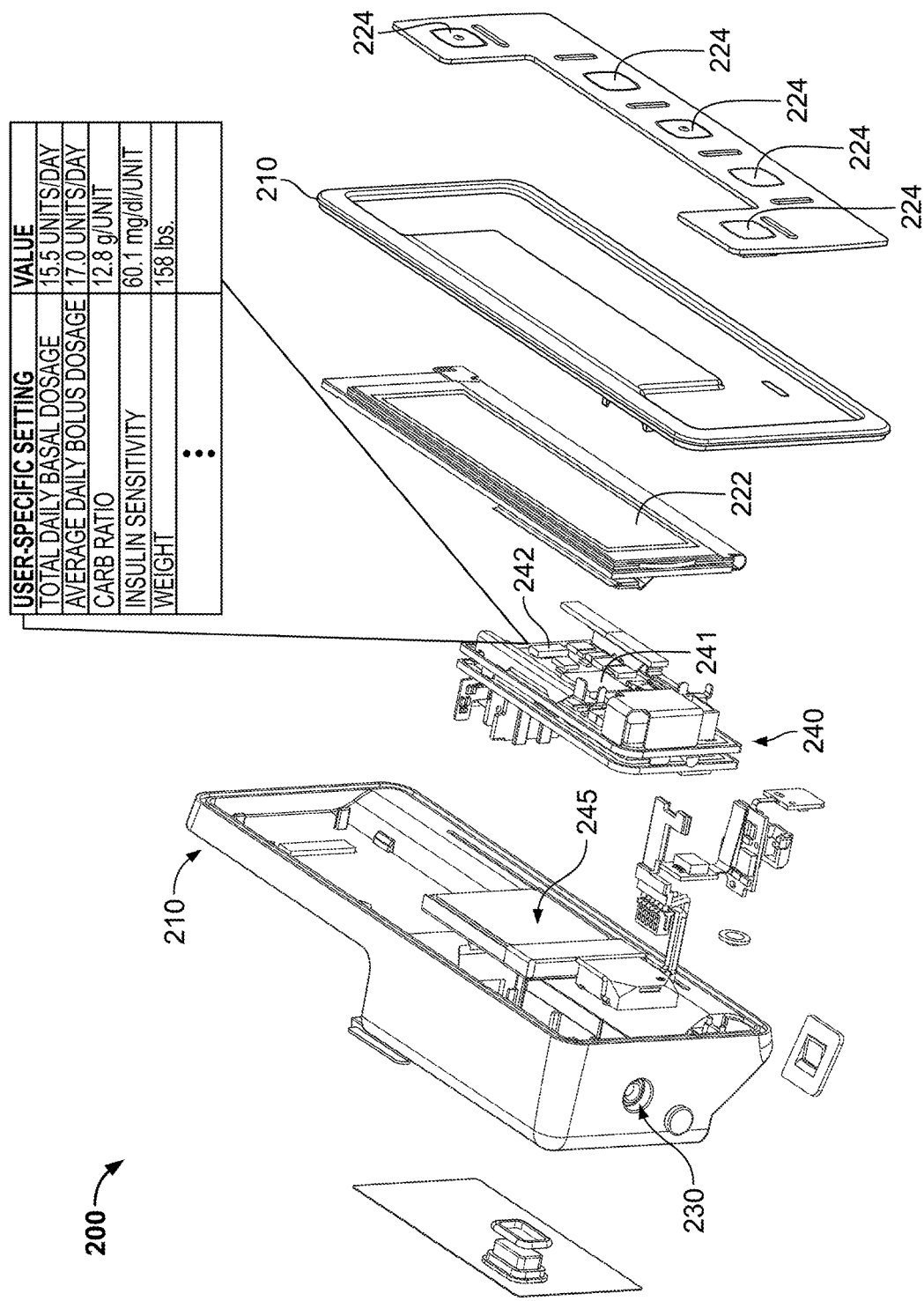
FIG. 5 is an exploded perspective view of a controller device for an infusion pump system, in accordance with some embodiments.

Referring now to FIG. 5, the controller device 200 (shown in an exploded view) houses a number of components that can be reused with a series of successive pump devices 100.

In particular, the controller device 200 can include control circuitry 240 and a rechargeable battery pack 245, each arranged in the controller housing 210. As described above, rechargeable battery pack 245 may provide electrical energy to components of control circuitry 240, other components of the controller device (e.g., a display device 222 and other user interface components, sensors, or the like), or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. At least one memory device 242 of the control circuitry may be configured to store a number of user-specific settings that are input via the user interface 220. For example, the control circuitry 240 can cause the memory device 242 to store any of the following user-specific settings: carbohydrate ratio, insulin sensitivity, scheduled total basal dose per day, and weight. Also, the control circuitry 240 can cause the memory device 242 to store any of the following parameters derived from the historical pump usage information: average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, frequency of using an auto-off alarm per day, and a frequency of cannula and tube primes per day. To the extent these aforementioned settings or historical parameters are not stored in the memory device 242, the control circuitry 240 can be configured to calculate any of these aforementioned settings or historical parameters from other data stored in the memory device 241 or otherwise input via the user interface 220.

The user interface 220 of the controller device 200 can include input components and/or output components that are electrically connected to the control circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the control circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The control circuitry 240 can be programmable to cause the control circuitry 240 to change any one of a number of settings for the infusion pump system 10. For example, the user may provide one or more instructions to adjust a number of settings for the operation of the infusion pump system 10. Such settings may be stored in one or more memory devices arranged in the control circuitry 240.

Still referring to FIG. 5, the infusion pump system 10 can be equipped with the inspection light device 230 to conveniently aid in visual inspection processes. For example, visual inspection and possible change of the infusion set 146 may be required in less than optimal conditions, including low-light conditions. Likewise, visual inspection of the pump housing cavity 116 (and the medicine cartridge 120 therein) may be required in low-light conditions. The user interface 220 of the controller device 200 can include an illuminated display screen 222 to facilitate the user's view of the display screen 222, but the inspection light device 230 provides a dedicated light source for illuminating targeted sites external to the controller device 200, for providing an alert notification, or a combination thereof. The inspection light device 230 can include one or more user triggered light sources that are positioned to direct illumination at targeted objects outside of the pump system 10 or at components of the pump device 100. In the embodiment depicted in FIG. 5, the light source is arranged on the controller device 200. Such an arrangement provides close proximity to the control circuitry 240 housed in the controller device 200, thereby permitting the light source of the inspection light device 230 to be electrically connected to the control circuitry. In other embodiments, could be arranged on the pump device 100 or on both the controller device 200 and the pump device 100. The inspection light device 230 can also be used to provide a visual notification to the user in the event of an alert or alarm condition. For example, as described further below in connection with FIGS. 7A-10 and 12A-13, the inspection light device 230 can be activated in response to the controller device 200 detecting a possible problem with the infusion set 146.

In some optional embodiments, the control circuitry 240 can include a cable connector (e.g., a USB connection port or another data cable port) that is accessible on an external portion of the controller housing 210. As such, a cable can be connected to the control circuitry 240 to upload data or program settings to the control circuitry or to download data from the control circuitry. For example, historical data of medicine delivery can be downloaded from the control circuitry 240 (via the cable connector) to a computer system of a physician or a user for purposes of analysis and program adjustments. Optionally, the data cable can also provide recharging power.

Figure 6:
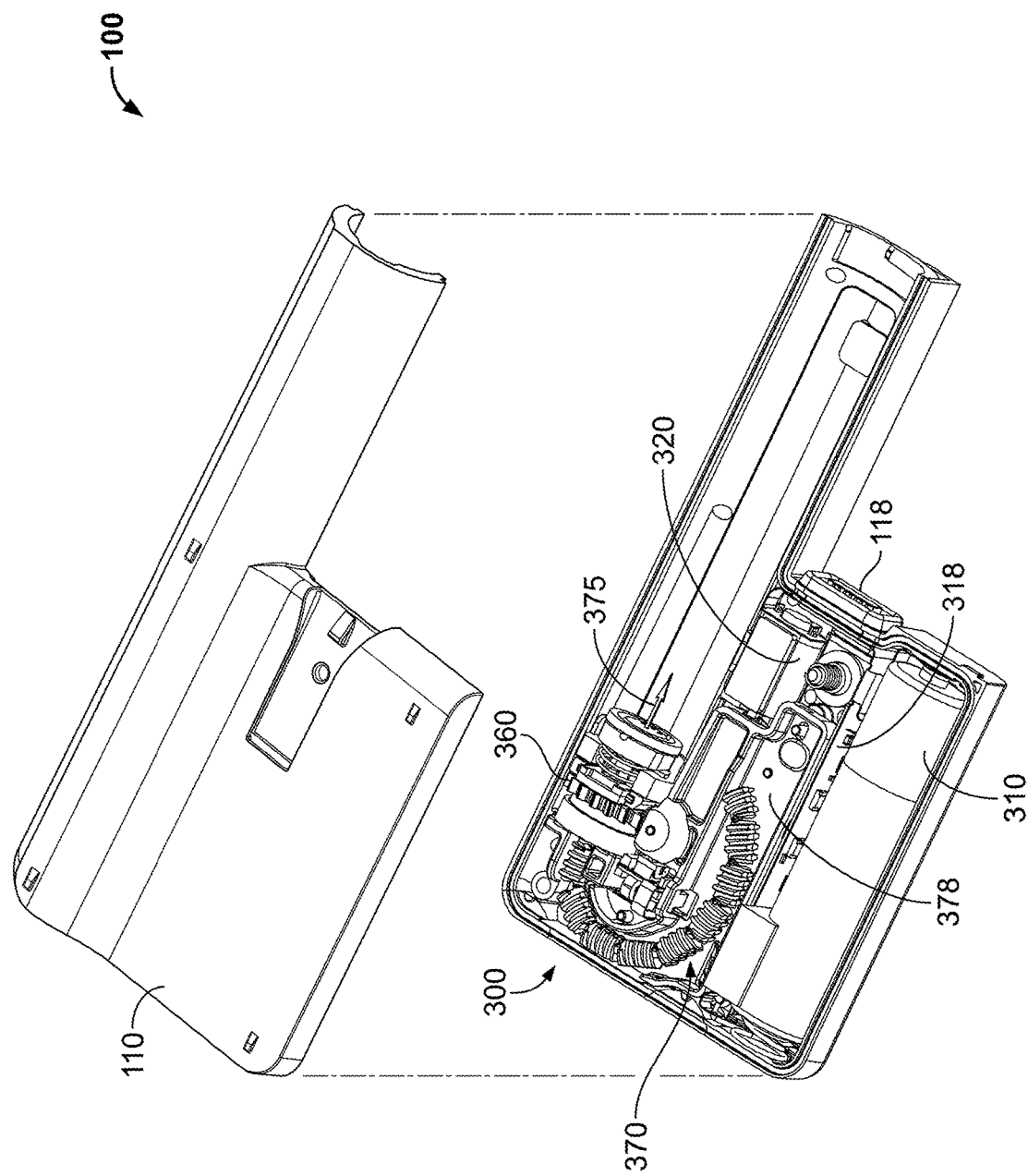
FIG. 6 is an exploded perspective view of the pump device of FIGS. 1-2 including a drive system detector, in accordance with some embodiments.

Referring now to FIG. 6, the pump device 100 can include a drive system 300 that is controlled by the controller device 200. As described in more detail below, the drive system 300 can incrementally dispense fluid in a controlled manner from the cartridge 120 (FIG. 2) inserted into the pump device 100. In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 (FIG. 5) when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 6, in some embodiment, the drive system 300 may include a number of components, such as an electrically powered actuator (e.g., reversible motor 320 or the like), a drive wheel 360, a flexible piston rod 370, and a plunger engagement device 375. In this embodiment, the reversible motor 320 drives a gear system (not shown in FIG. 6) to cause the incremental rotation of the drive wheel 360. For example, the drive wheel 360 can be incrementally rotated via a repeated motion of a ratchet mechanism actuated by the gear system coupled to the motor 320. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 6, the drive wheel 360 is the driver while the flexible piston rod 370 is the driven member. As further described below, the rotation of the drive wheel 360 can drive the flexible piston rod 370 forward in a linear longitudinal direction toward the medicine cartridge 120 (FIG. 2).

Figure 7A:
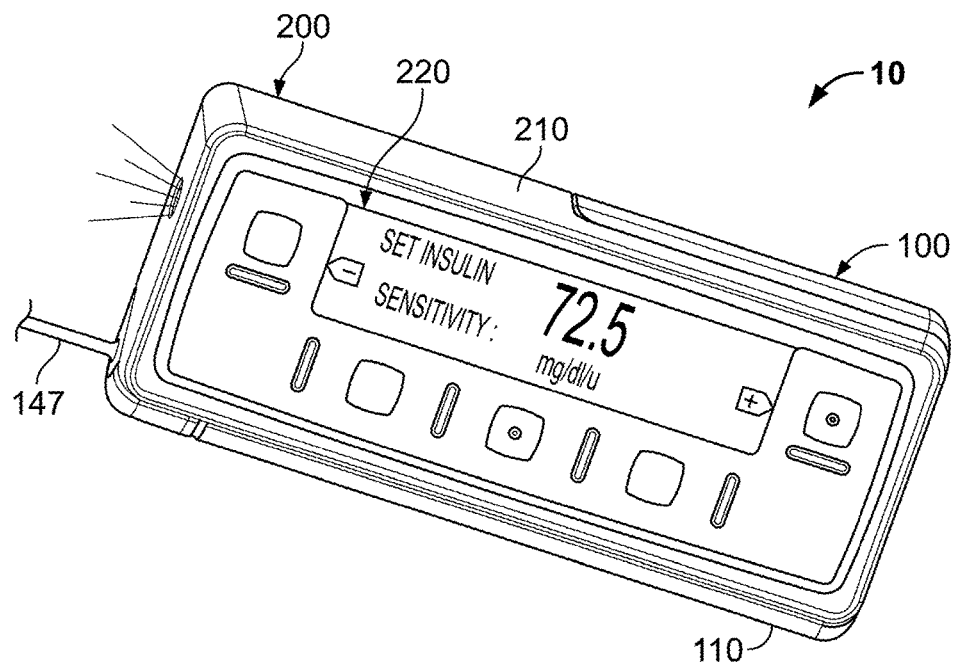
FIGS. 7A-B are perspective views of the infusion pump system of FIG. 1 including a user interface display for inputting a user-specific setting and an alert related to that user-specific setting, in accordance with some embodiments.
Figure 7B:
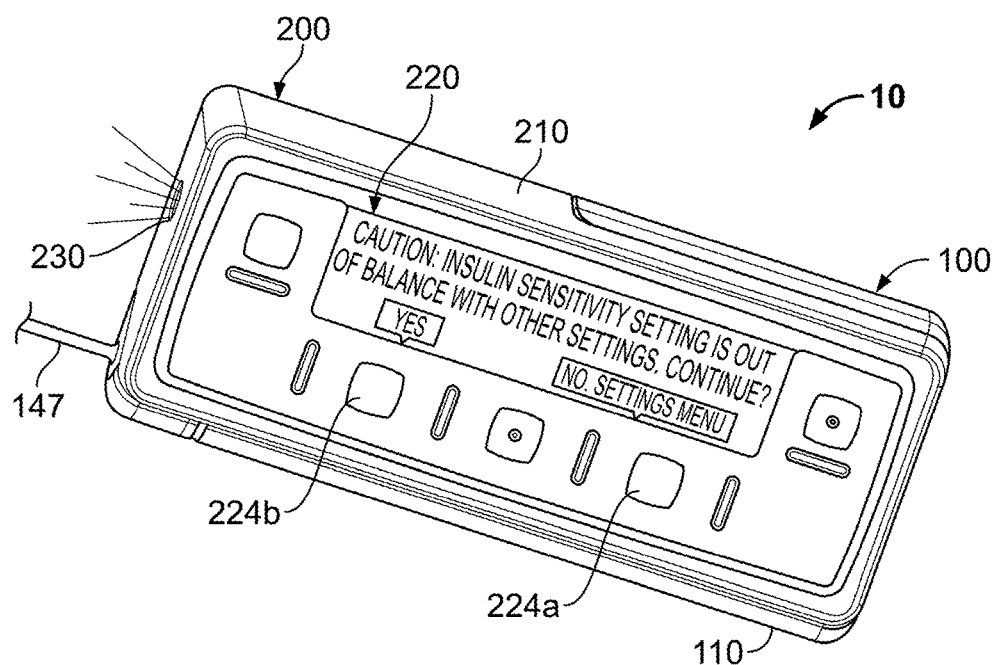

Referring now to FIGS. 7A-7B, the infusion pump system 10 can be configured to receive user input for one or more user-specific settings and to thereafter output an alert to the user if the newly input value for the user-specific setting is out of balance with one or more different user-specific settings stored by the pump system 10. For example, the user interface 220 can be employed to manually input any of the following user-specific settings: carbohydrate ratio, insulin sensitivity, scheduled basal dosages per day (e.g., basal profile), and weight. In the particular embodiment depicted in FIG. 7A, the user interface 220 is employed to input a new value for the insulin sensitivity (e.g., in units of mg/dL/insulin unit), which can be employed by the controller device 10 each time the user requests a calculation for a correction bolus dosage. Because this parameter may vary among different users, the parameter is a user-specific setting (e.g., one person's bodily response to a dosage of insulin can be quite different from another person's bodily response to the same dosage of insulin). The user may activate particular buttons 224 of the user interface 220 so as to select a particular menu option that prompts the user to input the new value for this particular setting. As shown in FIG. 7B, if the new value input by the user is out of balance with one or more different user-specific settings, the infusion pump system 10 can output an alert to the user. Example processes for determining whether the newly input value is out of balance with other settings are described in more detail below in connection with FIGS. 9-10. In this example, the alert is provided to the user in the form of a textual alert message and, optionally, an audible or vibratory alarm and a temporary illumination of the aforementioned flashlight instrument 230. In addition to providing the alert, the controller device 200 may also prompt the user to take a corrective action. For example, the user can select a button 224a that indicates the user does not want to continue with the possibly erroneous setting, which then causes the controller device to respond by displaying the menu option for inputting a new value for the user-specific setting (refer to FIG. 7A again). Alternatively, the user can select a button 224b indicating that the user wishes to continue with the newly input value for the setting, which will then silence the alert (either permanently or for a predetermined period of time, such as about 1 hour to about 96 hours, about 8 hours to about 48 hours, and preferably about 24 hours in this example).

Figure 8A:
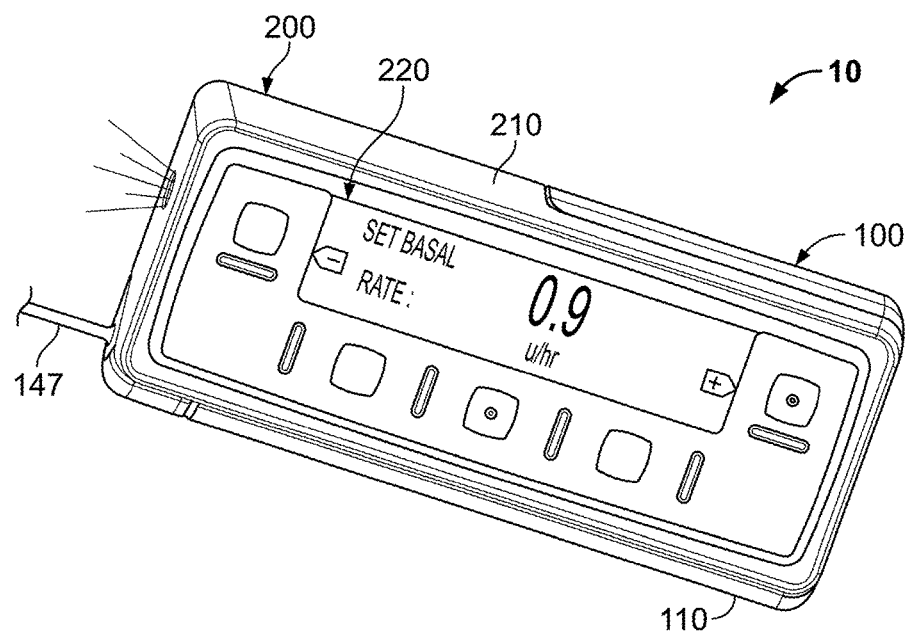
FIGS. 8A-B are perspective views of the infusion pump system of FIG. 1 including a user interface display for inputting another user-specific setting and an alert related to that user-specific setting, in accordance with some embodiments.
Figure 8B:
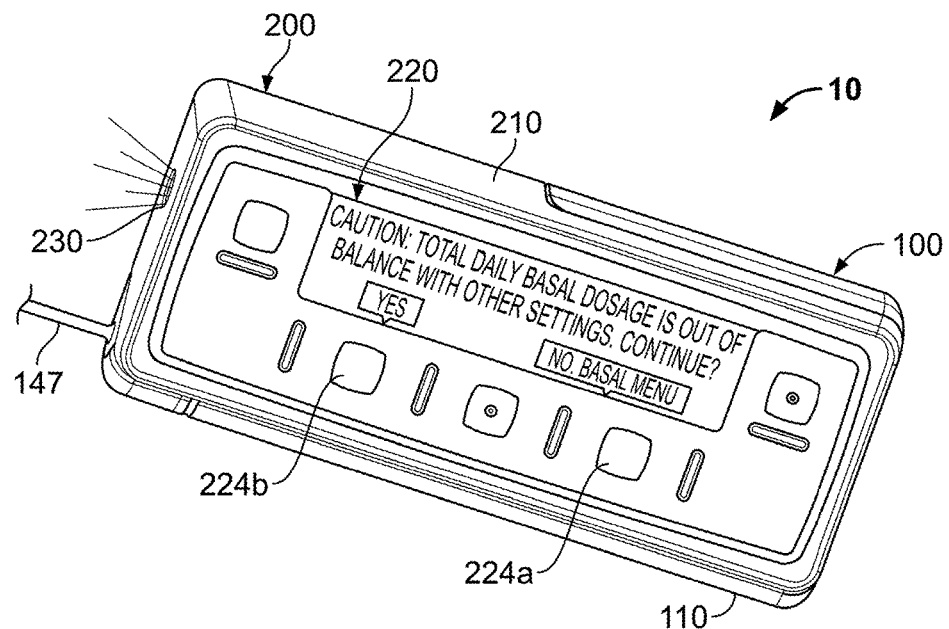

Referring now to FIGS. 8A-8B, the infusion pump system 10 can be configured to receive user input for one or more user-specific settings related to a daily basal dosage schedule (e.g., the user's basal profile) and to thereafter output an alert to the user if the newly input value for the scheduled amount of total daily basal dosages is out of balance with one or more different user-specific settings stored by the pump system 10. As previously described, the user interface 220 can be employed to manually input the scheduled basal dosage(s) per day, which may be a single basal rate over an entire 24-hour period or may be a set of different basal rates over an entire 24-hour period (e.g., a basal rate of 0.7 Units/hour from 12:00 am to 8:00 am, a basal rate of 0.8 Units/hour from 8:00 am to 4:00 pm, and yet another basal rate of 0.6 Units/hour from 4:00 pm to 12:00 am. Such a basal schedule can be stored by the controller device 200 and used to calculate the total daily basal dosage. Here again, this parameter may vary among different users, depending on the user's lifestyle, the user's bodily response to a dosage of insulin, and other factors. The user may activate particular buttons 224 of the user interface 220 so as to select a particular menu option that prompts the user to input the new value(s) for this particular setting. As shown in FIG. 8B, if the new value(s) input by the user create a total daily basal dosage that is out of balance with one or more different user-specific settings, the infusion pump system 10 can output an alert to the user. Again, example processes for determining whether the newly input value is out of balance with other settings are described in more detail below in connection with FIGS. 9-10. In this example, the alert is provided to the user in the form of a textual alert message and, optionally, an audible or vibratory alarm and a temporary illumination of the aforementioned flashlight instrument 230. In addition to providing the alert, the controller device 200 may also prompt the user to take a corrective action. For example, the user can select a button 224a that indicates the user does not want to continue with the possibly erroneous setting, which then causes the controller device to respond by displaying the menu option for inputting a new value for the basal dosage schedule (refer to FIG. 8A again). Alternatively, the user can select a button 224b indicating that the user wishes to continue with the newly input value for the setting, which will then silence the alert (either permanently or for a predetermined period of time, such as about 1 hour to about 7 days, about 8 hours to about 48 hours, and preferably about 24 hours in this example).

In addition or in the alternative, the infusion pump system 10 can be configured to output an alert to the user if a newly input value a particular basal rate for a portion of a day (not necessarily the total daily basal dosage) is out of balance with one or more different user-specific settings stored by the pump system 10. For example, if a basal rate for a particular user was previously set at 1.0 Units/hour of each day (resulting in a total daily basal dosage of 24 Units/day), a newly input value for a basal rate during only a small portion of the day (e.g., a newly input basal rate of 3 Units/hour for 3 hours from 1:00 pm to 4:00 pm) could cause possible user safety issues due to the significant surge in basal rate change over the short window of time. As such, some embodiments of the infusion pump system 10 can be configured to compare the different segments of the user's basal rate profile to any newly input values for a particular basal rate segment for purposes of identifying any segments of the basal profile that are out of balance with the other segments of the basal profile. For example, the infusion pump system 10 can identify that a newly input value of a particular basal rate segment is out of balance with the remaining portions of the basal profile when the newly input value includes a basal rate that is greater than twice the average basal rate (Units/hour) of the remaining portions of the basal profile, or that is greater than three times the average basal rate (Units/hour) of the remaining portions of the basal profile. In this example, the infusion pump system 10 can output an alert to the user in the form of a textual alert message and, optionally, an audible or vibratory alarm and a temporary illumination of the aforementioned flashlight instrument 230. In addition to providing the alert, the controller device 200 may also prompt the user to take a corrective action. For example, the user can select a button 224a that indicates the user does not want to continue with the possibly erroneous setting, which then causes the controller device to respond by displaying the menu option for inputting a new value for the basal dosage schedule.

Figure 9:
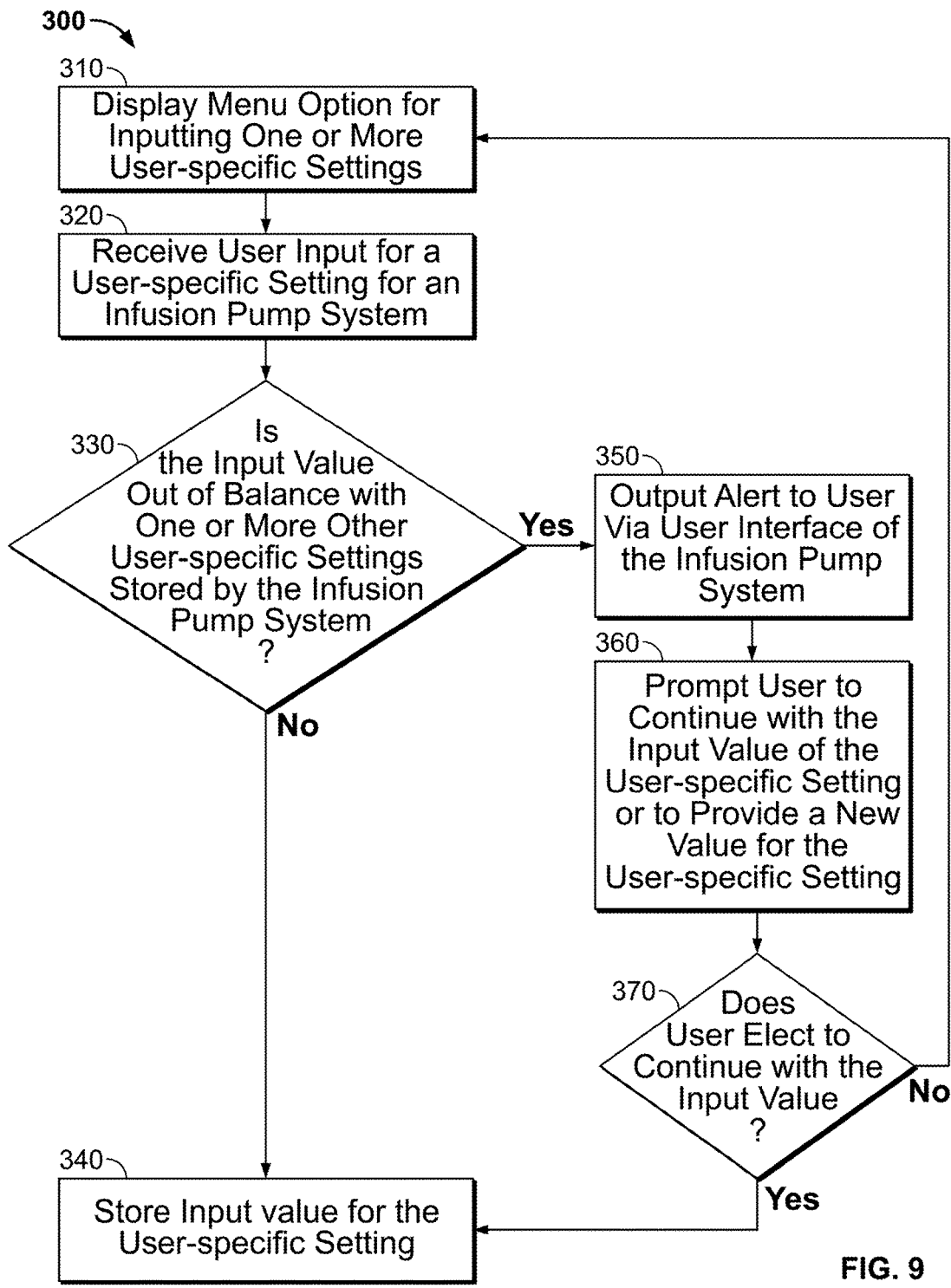
FIG. 9 is a process chart describing a method of controlling an infusion pump system, in accordance with some embodiments.

Referring now to FIG. 9, some embodiments of a method 300 for controlling an infusion pump system can be implemented so as to proactively monitor newly input values for user-specific settings and to alert a user if the newly input value is out of balance with one or more different user-specific settings previously stored by the infusion pump system. Such a method 300 can be implemented by any of infusion pump systems described herein.

The method 300 can include an operation 310 of displaying a menu option for inputting one or more user-specific settings. The menu option can be displayed via a user interface display screen of an infusion pump system (refer, for example, to FIGS. 7A and 8A). As previously described, a user may activated one or more buttons on a user interface of an infusion pump system so as to enter the selected menu option and thereby receive a prompt to input a new value for a particular user-specific setting.

The method can also include operation 320, wherein the infusion pump system receives user input for a user-specific setting for the infusion pump system. As previously described, the user interface of the infusion pump system can be employed to manually input any of the following user-specific settings: carbohydrate ratio, insulin sensitivity, scheduled basal dosages per day (e.g., basal profile), and weight.

Still referring to FIG. 9, the method 300 can also include the operation 330 in which the infusion pump system determines whether the newly input value of the user-specific setting is out of balance with one or more other user-specific settings stored by the infusion pump system. This operation 330 can include comparing the newly input value to a range of proper values calculated as a function of at least one of the different user-specific settings previously stored by the infusion pump system. For example, any newly input value for a carb ratio setting or an insulin sensitivity setting can be compared to the previously stored setting for the user's daily basal schedule (which provides the total daily basal dosage) as follows:

$$\text{Balanced Range for Carb Ratio} = [1.3*(\text{Weight})*(1-K)]/(\text{Basal}) \text{ to } [1.3*(\text{Weight})*(1+K)]/(\text{Basal}),$$

and $$\text{Balanced Range for Insulin Sensitivity} = [980(1-K)]/(\text{Basal}) \text{ to } [980(1+K)]/(\text{Basal}),$$

where: K=tolerance setting (e.g., 0.1 for an average pump user),

Weight=the user's weight in lbs.,
Basal=Total Daily Basal Dosage Amount (calculated from the user's basal profile) in Units of insulin,
Carb Ratio is in units of grams/Unit, and
Insulin Sensitivity is in units of mg/dl/Unit.

Also in this example, any newly input value for an insulin sensitivity setting or the user's daily basal schedule (which provides the total daily basal dosage) can be compared to the previously stored setting for the user's carb ratio as follows:

Balanced Range for Insulin Sensitivity=[754*(Carb Ratio)*(1−K)]/(Weight) to [754*(Carb Ratio)*(1+K)]/(Weight), and Balanced Range for Total Daily Basal Dosage=[1.3*(Weight)*(1−K)]/(Carb Ratio) to [1.3*(Weight)*(1+K)]/(Carb Ratio), where: K=tolerance setting (e.g., 0.1 for an average pump user),
Weight=the user's weight in lbs.,
Basal=Total Daily Basal Dosage Amount (calculated from the user's basal profile) in Units of insulin,
Carb Ratio is in units of grams/Unit, and
Insulin Sensitivity is in units of mg/dl/Unit.

Also in this example, any newly input value for a carb ratio setting or the user's daily basal schedule (which provides the total daily basal dosage) can be compared to the previously stored setting for the user's insulin sensitivity as follows:

Balanced Range for Carb Ratio=
(0.00133)*(Weight)*(Insulin Sensitivity)*(1−K) to (0.00133)*(Weight)*(Insulin Sensitivity)*(1+K), and Balanced Range for Total Daily Basal Dosage=
[980*(1−K)]/(Insulin Sensitivity) to [980*(1+K)]/(Insulin Sensitivity), where: K=tolerance setting (e.g., 0.1 for an average pump user),
Weight=the user's weight in lbs.,
Basal=Total Daily Basal Dosage Amount (calculated from the user's basal profile) in Units of insulin,
Carb Ratio is in units of grams/Unit, and
Insulin Sensitivity is in units of mg/dl/Unit.

Alternatively, this operation 330 can include comparing the newly input value to a look-up table stored by the infusion pump system that identifies a proper value (+/−a tolerance range) for the first user-specific setting based on the previously stored values for at least one of the different user-specific settings.

If the operation 330 yields a result in which the newly input value for the user-specific setting is not out of balance with the other user-specific settings (e.g., not outside of the balanced ranges shown in the functions above, not outside the proper corresponding value from the aforementioned look-up table, or the like), the method can continue to operation 340 in which the infusion pump system stores the newly input value for the user-specific setting. For example, the newly input value can be stored by the memory device 241 (FIG. 5) of the control circuitry 240 housed by the pump system 10.

If, however, the operation 330 yields a result in which the newly input value for the user-specific setting is out of balance with one or more of the other user-specific settings (e.g., the newly input value falls outside the balanced ranges shown in the functions above, falls outside the proper corresponding value from the aforementioned look-up table, or the like), the method can continue to operation 350 in which the infusion pump system outputs an alert to the user via a user interface. For example, the infusion pump system can output a textual alert message via a user interface display screen (refer, for example, to FIGS. 7B and 8B), which indicates to the user that the newly input value may be unsafe or otherwise erroneous. Optionally, the infusion pump system may also alert the user via an audible tone, a vibratory movement, an activation the flashlight illumination instrument 230, or a combination thereof.

Still referring to FIG. 9, the method 300 may also include the operation 360 in which the infusion pump system prompts the user either to continue with the newly input value that gave rise to the aforementioned alert or to reject the newly input value and provide a corrected value for the user-specific setting. For example, the infusion pump system may prompt the user to selected either button 224a or button 224b as shown in FIG. 7B or FIG. 8B.

As shown in operation 370, if the user indicates via the user interface that he or she elects to continue with the newly input value (e.g., to "override" or "ignore" the alert), the method 300 may continue to operation 340 in which the infusion pump system stores the newly input value for the user-specific setting. Such a selection from the user (e.g., indicating that the user wishes to continue with the newly input value for the setting) will then silence the alert either permanently or for a predetermined period of time, such as about 1 hour to about 96 hours, about 8 hours to about 48 hours, and preferably about 24 hours in one example.

Alternatively, as shown in operation 370, if the user indicates via the user interface that he or she will not continue with the newly input value, the method 300 may return to operation 310 in which the infusion pump displays the aforementioned menu option that prompts the user to input a new (corrected) value for the particular user-specific setting. As previously described, the menu option can be displayed via a user interface display screen of an infusion pump system (refer, for example, to FIGS. 7A and 8A).

Still referring to FIG. 9, it should be understood from the description herein that the infusion pump system can implement the method 300 and additionally provide a number of convenient options to the user when the alert (operation 350) is output to the user. For example, the content of textual alert message can vary by the degree of imbalance or by the particular user-specific setting that is out of balance. Additionally, some embodiments of the infusion pump system can be configured to provide the user with an option to temporarily silence or disable the aforementioned alert for a limited period of time (e.g., about 1 minute to about 60 minutes, about 5 minutes to about 20 minutes, and preferably about 10 minutes), after which the infusion pump system would again prompt the user with the same alert (e.g., repeat operation 350). In such circumstances, the limited period of time during with the alert is silenced can vary (e.g., the frequency of the alert output from the infusion pump system can vary) depending upon the degree of imbalance or by the particular user-specific setting that is out of balance. Furthermore, some embodiments of the infusion pump system can be configured to prevent the user from continuing with the newly input value for the user-specific setting that is out of a balanced range with a different one of the user-specific setting (e.g., preventing the operation 370 and thereby by requiring the user to accept the originally stored value or to input a corrected value at operation 310). Additionally, in some embodiments, the level of imbalance tolerated can be adjustable (e.g., the tolerance factor K in the functions listed above can be adjusted) in response to user input from a clinician or the user.

Figure 10:
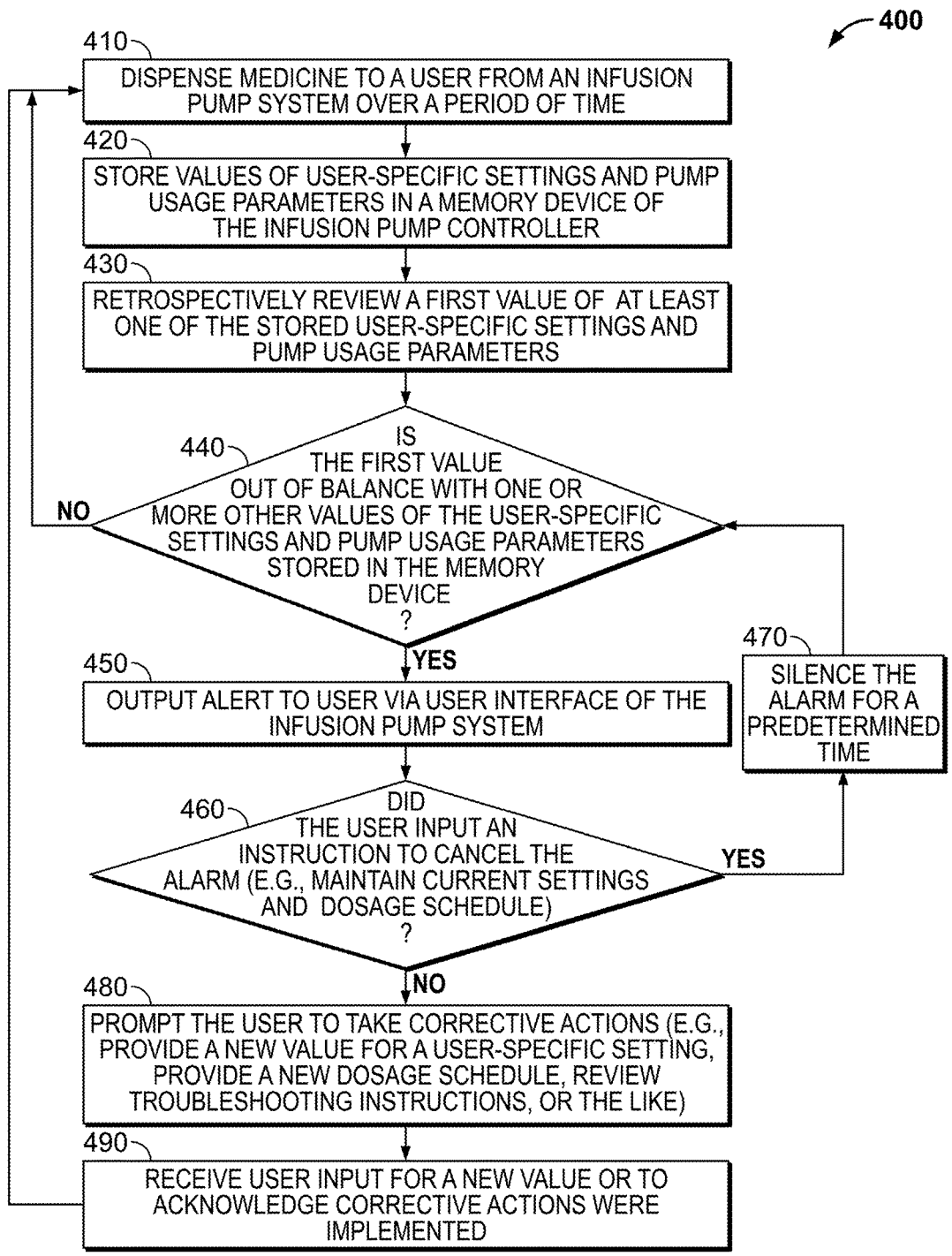
FIG. 10 is a process chart describing a method of controlling an infusion pump system, in accordance with some embodiments.

Referring now to FIG. 10, some embodiments of a method 400 for controlling an infusion pump system can be implemented so as to retrospectively evaluate a previously stored value of user-specific settings and pump usage information to thereby alert the user if any of the values is out of balance with a different user-specific setting or pump usage value. Such a method 400 can be implemented by any of infusion pump systems described herein.

The method 400 can include an operation 410 of dispensing medicine to a user from an infusion pump system over a period of time. For example, the infusion pump system 10 can dispense insulin to a user in a combination of basal and bolus dosages over a period of days. In operation 420, the infusion pump system can store values of a number of user-specific settings and pump usage parameters. For example, as previously described, the memory device of the control circuitry 240 can be configured to store at least the following user-specific settings: carbohydrate ratio, insulin sensitivity, the user's weight, and the user's daily basal schedule (which indicates the user's total daily basal dosage). Additionally, the memory device of the control circuitry 240 can be configured to store any of the following pump usage parameters: average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, frequency of using an auto-off alarm per day, and a frequency of cannula prime operations and tube prime operations per day.

Still referring to FIG. 10, the method 400 can include operation 430 in which the infusion pump system retrospectively evaluates a presently stored value of one of the aforementioned user-specific settings and the pump usage parameters. For example, the presently stored value for the selected one of these aforementioned settings or parameters can be analyzed by the controller device to determine whether there is a possible imbalance in a user-specific setting, a possible improper use of the pump system, or both. In operation 440, the infusion pump system determines whether the first value of the selected settings or parameters is out of balance with one or more other settings or parameters stored in the memory device (refer to operation 420). For example, the infusion pump system can identify an improper pump usage by comparing the average total basal dose per day, average total bolus dose per day, as follows:

Balanced Range for Bolus=(Basal)*[(0.5−$K$)/(0.5+$K$)] to (Basal)*[(0.5+$K$)/(0.5−$K$)], Where: Bolus=average total bolus dose per day,
Basal=average total basal dose per day (or, alternatively, the user's total daily basal dosage as calculated from the user's daily basal schedule), and
$K$=tolerance setting (e.g., 0.1 for an average pump user).

Balanced Range for Basal=(Bolus)*[(0.5−$K$)/(0.5+$K$)] to (Bolus)*[(0.5+$K$)/(0.5−$K$)], Where: Bolus=average total bolus dose per day,
Basal=average total basal dose per day (or, alternatively, the user's total daily basal dosage as calculated from the user's daily basal schedule), and
$K$=tolerance setting (e.g., 0.1 for an average pump user).

Thus, in this example, if the average total daily bolus dosage is significantly greater than the average total daily basal dosage, the infusion pump device can be configured to determine that the user may be over compensating for a lack of basal dosages using an elevated amount of correction bolus dosages throughout the day.

Also in this example for operation 440, the infusion pump system can identify an improper pump usage by comparing average total daily dose to each of the average total basal dose per day and average total bolus dose per day, as follows:

Balanced Range for Basal=(0.5−$K$)(Total Daily Dose) to (0.5+$K$)(Total Daily Dose), Where: Total Daily Dose=average total daily dose (combined bolus and basal),
Basal=average total basal dose per day (or, alternatively, the user's total daily basal dosage as calculated from the user's daily basal schedule), and
$K$=tolerance setting (e.g., 0.1 for an average pump user).

Balanced Range for Bolus=(0.5−$K$)(Total Daily Dose) to (0.5+$K$)(Total Daily Dose), Where: Total Daily Dose=average total daily dose (combined bolus and basal),
Bolus=average total bolus dose per day, and
$K$=tolerance setting (e.g., 0.1 for an average pump user).

Thus, in this example, if the average total daily bolus dosage is a significant majority of the average total daily dose, the infusion pump device can be configured to determine that the user may be over compensating for a lack of basal dosages using an elevated amount of correction bolus dosages throughout the day (or that the presently stored value for the insulin sensitivity value is inaccurate).

Additionally in this example for operation 440, the infusion pump system can identify an improper pump usage if the frequency of cannula priming operations is out of balance with the frequency of tube priming operations. In particular, the infusion pump system can be configured to perform two different types of priming operations (cannula prime and tubing prime). A tubing prime is an operation that occurs before the infusion set 146 is attached to the user's skin. During this tubing prime operation, the pump system dispenses medicine through the tube 147 of the infusion set 146 until the medicine exits the cannula tip (e.g., a drop of medicine appears out of the cannula tip). The cannula priming operation is generally performed after the cannula tip of the infusion set 146 is inserted through a penetration point of the user's skin. The cannula priming operation is usually performed for the purpose of backfilling the empty space in the infusion set cannula that might exist after insertion through the skin penetration point, and it is typically significantly smaller than the tubing prime operation. Here, the infusion pump system can identify an improper pump usage by comparing number of cannula prime operations (as stored in the pump usage information) to the number of tubing prime operations (also as stored in the pump usage information), as follows:

Balanced Range for Cannula Prime Operations= (Tubing Prime Operations)*[(0.5−$K$)/(0.5+$K$)] to (Tubing Prime Operations)*[(0.5+$K$)/(0.5−$K$)], Where: Cannula Prime Operations=the number of cannula prime operations in a given time period (e.g., about 1 to about 3 days), Tubing Prime Operations=the number of tubing prime operations in a given time period (e.g., about 1 to about 3 days), and K=tolerance setting (e.g., 0.1 for an average pump user).

Thus, if the number of tubing prime operations are significantly less than number of cannula prime operations during the same period of time, the infusion pump device can be configured to determine that the user may be improperly using tubing prime operations during setup of each new infusion set 146. Additionally or alternatively, the number of tubing prime operations and the number of cannula prime operations can be compared to a predefined limit for a particular time period (e.g., 0 to 3 tubing prime operations for each four-day period, 0 to 1 tubing prime operation for each two-day period, or the like; and 0 to 3 cannula prime operations for each four-day period, 0 to 1 cannula prime operation for each two-day period, or the like). Additionally or alternatively, for those embodiments in which the pump system 10 employs a disposable pump device 100, the number of tubing prime operations and the number of cannula prime operations can be compared to a predefined limit for each new pump device 100 that is attached to the controller device 200 (e.g., 1 to 4 tubing prime operations for each new pump device 100, preferable 1-2 tubing prime operations for each new pump device 100; and 1 to 4 cannula prime operations for each new pump device 100, preferable 1-2 cannula prime operations for each new pump device 100). Furthermore, it should be understood from the description herein that, in some, embodiments, the "number of tubing prime operations" used in the aforementioned comparisons/calculations would exclude any tubing prime operations were initiated in response to an alarm of the pump system 10 (e.g., such as a tubing occlusion alarm).

It should be understood from the description herein that the infusion pump system can be configured to perform the retrospective safety check of the pump usage parameters and user-specific settings by comparing any two or more the following stored values: average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, frequency of using an auto-off alarm per day, a frequency of cannula prime operations and tube prime operations per day, the user's carbohydrate ratio, the user's insulin sensitivity, the user's weight, and the user's daily basal schedule (which indicates the user's total daily basal dosage).

Still referring to FIG. 10, if the operation 440 yields a result in which the first value of the selected settings or parameters is not out of balance with one or more other settings or parameters stored in the memory device, the method can return to operation 410 in which the infusion pump system dispenses the medicine in accordance with normal usage.

If, however, the operation 440 yields a result in which the first value of the selected settings or parameters is out of balance with one or more other settings or parameters stored in the memory device, the method can continue to operation 450 in which the infusion pump system outputs an alert to the user via a user interface. For example, the infusion pump system can output a textual alert message via a user interface display screen, which indicates to the user that the particular pump setting or usage parameter is out of a balanced range. Optionally, the infusion pump system may also alert the user via an audible tone, a vibratory movement, activation the flashlight illumination instrument 230, or a combination thereof.

As shown in operation 460, if the user indicates via the user interface that he or she elects to cancel the alarm that was output in operation 450 (e.g., to "override" or "ignore" the alert), the method 400 may continue to operation 470 in which the alarm is silenced for a predetermined period of time. Such a selection from the user will then silence the alarm for a predetermined period of time, such as about 1 hour to about 96 hours, about 8 hours to about 48 hours, and preferably about 24 hours in one example.

Alternatively, as shown in operation 460, if the user does not indicate via the user interface that he or she elects to cancel the alarm, the method 400 may continue to operation 480 in which the infusion pump system prompts the user to take one or more corrective actions. The particular corrective actions prompted by the infusion pump system can be dependent upon which particular selected setting or parameter is out of balance with one or more other settings or parameters stored in the memory device. For example, if the pump usage parameters stored in the memory device reveal that the average total daily bolus dosage is significantly greater than the average total daily basal dosage, the infusion pump device can prompt the user to increase that basal dosage throughout the day, to increase the value for the user's carb ratio setting, to increase the value for the user's insulin sensitivity setting (refer to FIG. 7A), or a combination thereon. In another example, if the pump usage parameters stored in the memory device reveal that the number of tubing prime operations per day are significantly less than number of cannula prime operations per day, the infusion pump device can prompt the user to view a "troubleshoot" instruction guide (e.g., displayed on the user interface screen) that instructs the user on how to properly perform tubing prime operations during setup of each new infusion set 146.

The method 400 may also include operation 490 in which the infusion pump system receives user input in response to the prompting at operation 480. For example, the infusion pump system can receive user input at operation 490 when the user provides a new value to replace one or the aforementioned settings. In another example, the infusion pump system can receive user input at operation 490 when the user activates a button to acknowledge that the aforementioned troubleshooting instruction guide was viewed.

From there, the method 400 can return to operation 410 in which the infusion pump system dispenses the medicine in accordance with normal usage.

Figure 11:
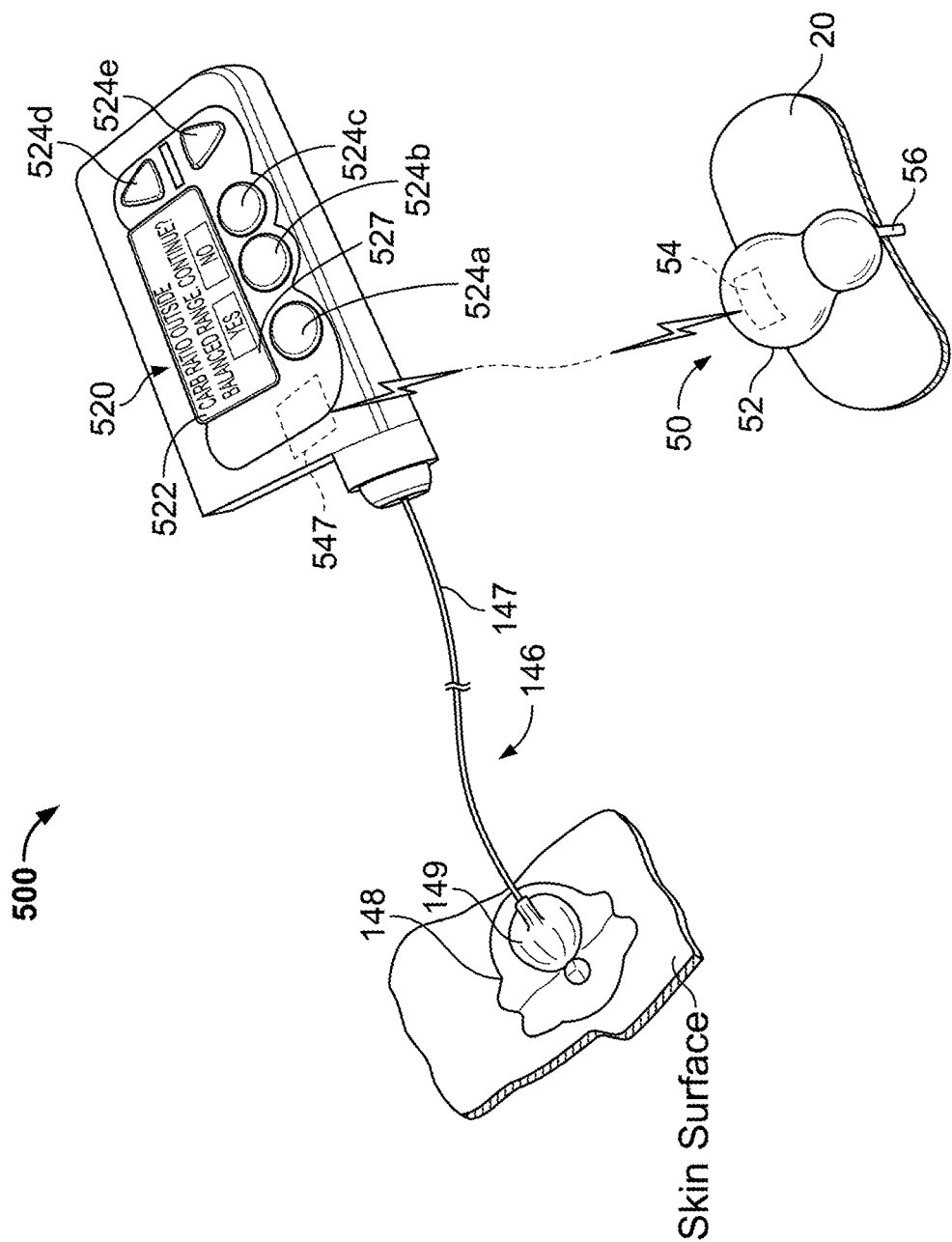
FIG. 11 is a perspective view of an alternative infusion pump system configured to respond to user input of value for a particular setting, in accordance with some embodiments.

Referring now to FIG. 11, some embodiments of a portable infusion pump system 500 employing one or more of the aforementioned safety features (e.g., similar to those depicted in any of FIGS. 7A-10) can employ a reusable pump apparatus (rather than a disposable pump device as previously described). In such circumstances, the infusion pump system 500 may comprise a reusable device that houses the control circuitry and the pump drive system within a single housing construct. In the particular embodiment depicted in FIG. 11, the pump system 500 comprises a reusable pump device that houses both the control circuitry and the pump drive system (which may include a piston rod and one or more gears). Similar to previously described embodiments, the pump system 500 can include a housing structure that defines a cavity in which a medicine cartridge can be received (not shown in FIG. 11; refer for example to cartridge 120 in FIG. 2). For example, the pump system 500 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 500 on the user's skin under clothing or in the user's pocket while receiving the medicine dispensed through the infusion set 146.

The pump system 500 can also communicate with the aforementioned glucose monitoring device 50 for the purpose of receiving data indicative of a user's blood glucose level. Similar to previously described embodiments, the pump system 500 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit. As shown in FIG. 11, the glucose monitoring device 50 can include the housing 52, the wireless communication device 54, and the sensor shaft 56 (similar to the embodiment described in connection with FIG. 1). In response to the measurements made by the sensor shaft 56, the glucose monitoring device 50 can employ the wireless communication device 54 to transmit data to a corresponding wireless communication device 547 housed in the pump system 500.

Still referring to FIG. 11, similar to previously described embodiments, the infusion pump system 700 may be configured to perform proactive or retrospective safety checks (e.g., refer to FIGS. 9 and 10) for the user-specific settings and pump usage parameters stored in one or more memory devices housed in the pump system 700. The user interface 520 of the pump system 500 includes a display device 522 and one or more user-selectable buttons 524a-e. The display device 522 can include an active area in which numerals, text, symbols, images, or a combination thereof can be displayed (as shown, for example, in FIG. 11). In one example, the display device 522 can be used to communicate to the user that a newly input value for a user-specific setting (e.g., the carb ratio in this example) is out of balance with one or more other user-specific settings, similar to the embodiments described in connection with FIGS. 7A-B, 8A-B, and 9). Thus, the pump device 500 can be configured to implement the proactive review of newly input values for user-specific settings as described in the method 300 in connection with FIG. 9. Likewise, the pump device 500 can be configured to implement the retrospective review of values for user-specific settings and pump usage parameters as described in the method 400 in connection with FIG. 10.

Also, the display device 522 can be used to communicate a number of settings or menu options for the infusion pump system 500. For example, the display device 522 can be used to communicate medicinal delivery information, such as the basal delivery rate, a bolus dosage, a historical record of medicine delivered, the amount of medicine remaining in the cartridge, or the like. In another example, the display device 522 can be used to communicate time and date information, which can be used by the user to determine dosage schedules, bolus delivery times, meal times, or the like. In such circumstances, the user may press one or more of the buttons 524a, 524b, 524c, 524d, and 524e to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 500 by pressing one or more buttons 524a, 524b, 524c, 524d, and 524e of the user interface 520. Thus, the user can contemporaneously monitor the operation of the pump system 500, including any messages pertaining to the proactive or retrospective safety checks (e.g., refer to FIGS. 9 and 10) from the same user interface 520.

Figure 12A:
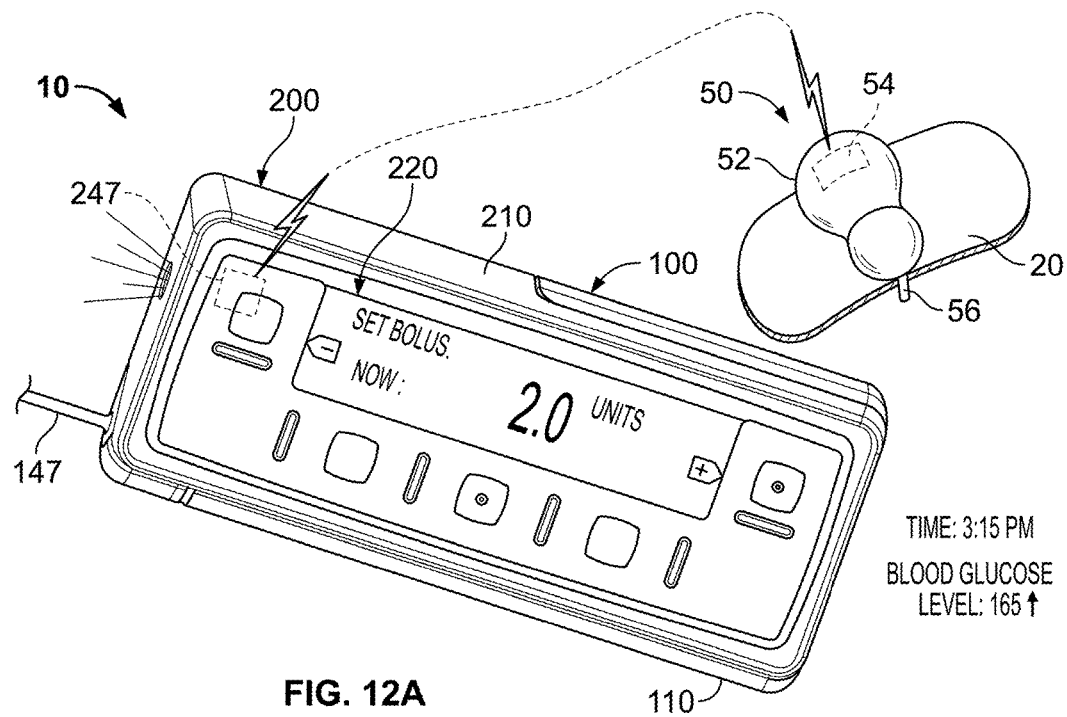
FIGS. 12A-B are perspective views of the infusion pump system of FIG. 1 including a user interface display for inputting a bolus dosage and an alert related to an infusion set device, in accordance with some embodiments.
Figure 12B:
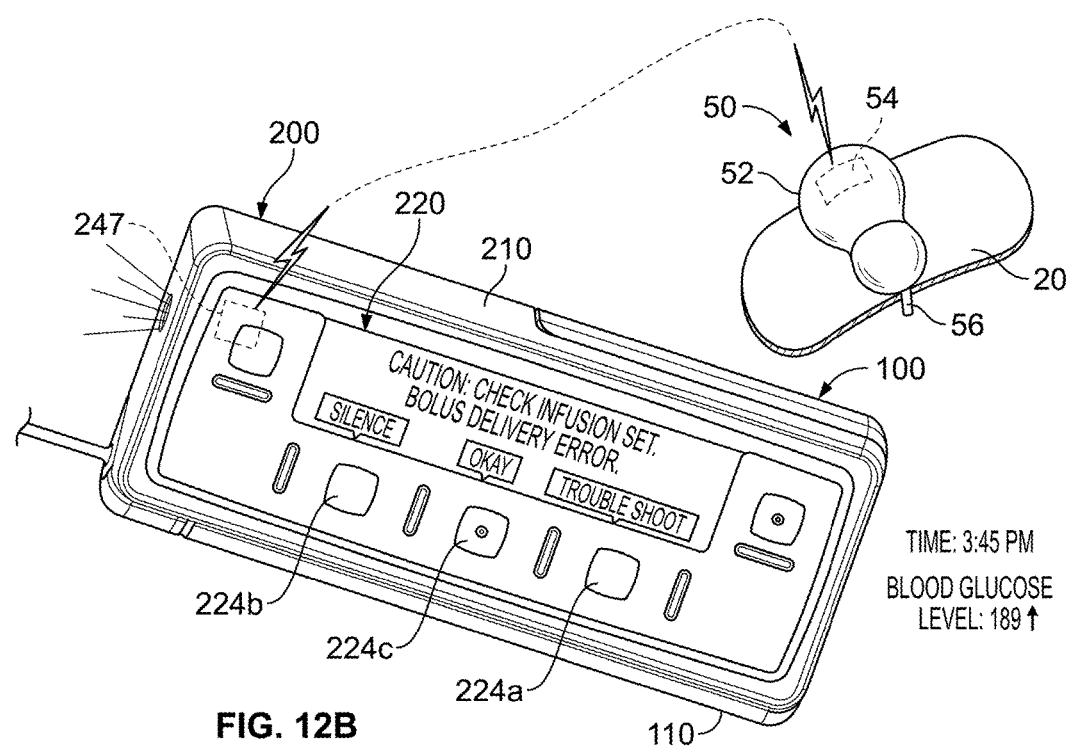

Referring now to FIGS. 12A-B, the infusion pump system 10 (as previously described in FIGS. 1-6) can configured to determine whether the dispensed medicine is being properly transferred from the infusion set 146 into the user's body, and such a determination can be based at least in part upon data communicated to the pump system 10 which is indicative the user's blood glucose levels over a period of time. Accordingly, the infusion pump system 10 can alert the user to a potential problem with an infusion set 146 (e.g., the insulin set cannula 149 is not properly seated on the skin, or the like) based at least in part on an analysis of the user's blood glucose levels during a period of time after medicine is dispensed from the infusion pump reservoir (e.g., cartridge 120 in FIG. 2). In one example, the infusion pump system can output an alert indicative of a possible problem with the infusion set 146 in response to a computational evaluation of the user's blood glucose levels over a predetermined period of time (e.g., about 15 minutes to about 75 minutes, preferably about 30 minutes to about 60 minutes) after initial dispensation of a bolus dosage. If the user's blood glucose levels are not decreasing (or, in some embodiments, if the rate of change of the user's blood glucose levels is not decreasing) during that predetermined time period, then the infusion pump system 10 can output an alert indicative of a potential problem with the infusion set 146 and may furthermore prompt the user to replace the infusion set 146 or otherwise provide troubleshooting instructions to the user.

In the particular example depicted in FIG. 12A, the user interface 220 is used to input a new value for a bolus dosage, and this input option screen can be employed by the controller device 200 each time the user requests a correction bolus dosage or a meal bolus dosage. In some embodiments, the controller device 200 can be configured to suggestion a recommended bolus amount to the user, which is then displayed on the user interface 220 for the use to accept (and thereby initiate the bolus dosage) or to modify to a different value before initiating the bolus dosage. The user may activate particular buttons 224 of the user interface 220 so as to select a particular menu option that prompts the user to input the new value for this particular setting. As shown in FIG. 12A, in this example, the present time is 3:15 PM and the user's recent blood glucose level was measured at 165 mg/dL and increasing (as indicated by the upward arrow). This blood glucose information can be received by wireless communication device 247 of the controller device 200 from the glucose monitoring device 50 or another blood glucose measurement device (e.g., a blood strip reader), as previously described. Alternatively, the blood glucose information can be manually input into the controller device 200 by the user (e.g., during the bolus suggestion calculation as previously described).

As shown in FIG. 12B, after the bolus dosage (as selected in FIG. 12A) is initiated, the infusion pump system 10 can cause the bolus of insulin or other medication to be dispensed from the reservoir (e.g., cartridge 120 in FIG. 2 in this embodiment) and through the infusion set tubing 147. In this example, the present time is now 3:45 PM (about 30 minutes after the bolus dosage was initiated in FIG. 12A)

and the user's recent blood glucose level was measured at 189 mg/dL and increasing (as indicated by the upward arrow). In such circumstances, the infusion pump system 10 can employ the blood glucose data wirelessly communicated or otherwise input to the pump system 10 to detect a potential problem with an infusion set 146 (e.g., the insulin set cannula 149 is not properly seated on the skin, or the like). Referring to the example in FIG. 12B, the infusion pump system 10 can output an alert indicative of a possible problem with the infusion set 146 in response to a pattern of the user's blood glucose levels over a predetermined period of time (e.g., about 15 minutes to about 75 minutes, preferably about 30 minutes to about 60 minutes in this embodiment) after initial dispensation of a bolus dosage. In this example, the alert is provided to the user in the form of a textual alert message and, optionally, an audible or vibratory alarm and a temporary illumination of the aforementioned flashlight instrument 230.

In this example, the alert is output to the user in response to the controller device 200 determining that user's blood glucose levels are not decreasing within the predetermined period of time and that the rate of change of the user's blood glucose levels is also not decreasing. In alternative embodiments, the controller device 200 can output the alert in response to determining that the rate of change of the user's blood glucose levels is not decreasing during the predetermined period of time (e.g., regardless of whether the actual blood glucose levels have increased or decreased). The infusion pump system 10 can output the alert indicative of a potential problem with the infusion set 146 and may furthermore prompt the user to take one or more corrective actions. For example, the user interface 220 of the infusion pump system can prompt the user to replace the infusion set 146, to review a troubleshooting guide (e.g., displayed on the user interface 220 or on another external device), or a combination thereof. For example, the user can select a button 224c that indicates the user has replaced the infusion set 146 with a newly seated infusion 146 or otherwise verified the infusion set 146 is properly secured at the skin penetration point. Alternatively, the user can select a button 224a that indicates the user is requesting troubleshooting instructions, which then display to the user a series of questions and instructions for the user to identify possible errors with the infusion pump system 10 or the infusion set 146 that might have caused the previously initiated bolus dosage to be less effective than desired. Alternatively, the user can select a button 224b indicating that the user wishes to the silence the alert (either because the user is currently satisfied with the blood glucose information or because there is a need to temporarily silence the infusion pump system), which will then silence the alert (either permanently or for a predetermined period of time, such as about 10 minutes to about 120 minutes hours, about 20 minutes hours to about 90 minutes, and preferably about 60 minutes in this example).

Figure 13:
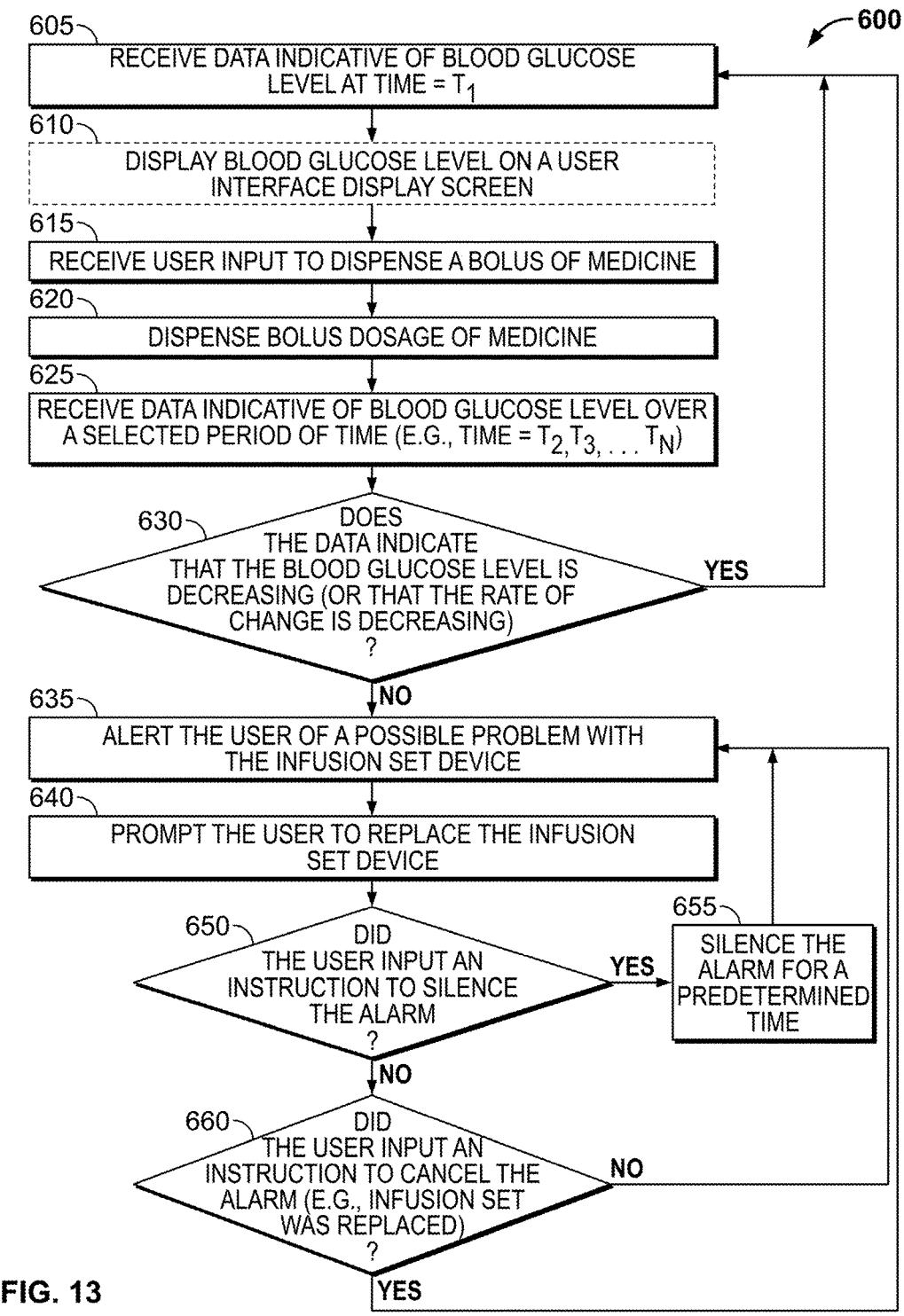
FIG. 13 is a process chart describing a method of controlling an infusion pump system, in accordance with some embodiments.

Referring now to FIG. 13, some embodiments of a method 600 for controlling an infusion pump system can be implemented so as to determine whether the dispensed medicine is being properly transferred from the infusion pump system and into the user's body. As previously described, such a determination in the method 600 can be based at least in part upon data communicated to the pump system 10 which is indicative the user's blood glucose levels over a selected period of time. The method 600 can be implemented by any of infusion pump systems described herein.

The method 600 can include an operation 605 of receiving data indicative of a blood glucose level at time $t_1$. As previously described, the blood glucose data (which may be indicative of a recent blood glucose level of the user) can be wirelessly received by the controller device 200 of the infusion pump system 10 from the glucose monitoring device 50 (FIGS. 12A-B) or another blood glucose measurement device (e.g., a blood strip reader). Alternatively, the blood glucose data can be manually input into the controller device 200 by the user via the user interface 220.

Optionally, the method 600 may include operation 610 in which the most recent blood glucose level is displayed on the user interface display screen of the pump system. For example, the infusion pump system 10 can be configured to display of the user interface 220 the user's blood glucose level along with an indication of whether the blood glucose level is increasing or decreasing.

The method 600 may also include operation 615 in which the infusion pump system receives user input to dispense a bolus dosage of the medicine. In one example, as previously described in connection with FIG. 12A, the user interface 220 can be employed to input a new value for a bolus dosage. This menu option can be displayed can by the controller device 200 each time the user requests a correction bolus dosage or a meal bolus dosage. In some embodiments, the controller device 200 can be configured to suggestion a recommended bolus amount to the user, which is then displayed on the user interface 220 for the use to accept (and thereby initiate the bolus dosage) or to modify to a different value before initiating the bolus dosage.

Still referring to FIG. 13, the method 600 can include the operation 620 of dispensing the bolus dosage of the medicine, which may be performed in response to operation 615. For example, the infusion pump system 10 can activate the drive system 300 over a period of time to thereby cause the bolus of insulin or other medication to be dispensed from the reservoir (e.g., cartridge 120 in FIG. 2 in this embodiment) and through the infusion set tubing 147.

The method 600 can also include the operation 630 of receiving data of the blood glucose level over a period of time. For example, the blood glucose data (which may be indicative of a recent blood glucose level of the user) can be wirelessly received by the controller device 200 of the infusion pump system 10 from the glucose monitoring device 50 (FIGS. 12A-B) every ten minutes. Thus, the period of time for receiving the additional blood glucose data can include multiple data points at time $t_2, t_3, \ldots t_n$. Alternatively, the additional blood glucose data may be received only one additional time ($t_2$) during a selected period of time after the bolus dosage was initiated. In any of these examples, the operation 630 causes the infusion pump system 10 to gather additional data so that the pump system 10 can store and evaluate the user's blood glucose levels over a predetermined period of time.

In operation 630, the infusion pump system determines whether the blood glucose level data indicates that the user's blood glucose level is decreasing, that the rate of change of the user's blood glucose level is decreasing, or both. For example, the controller device 200 of the pump system 10 can evaluate the user blood glucose level a times $t_1, t_2, t_3, \ldots t_n$ (as received and stored during operations 605 and 625) to determine that the user's blood glucose level is trending lower or higher during the predetermined period of time (e.g., about 15 minutes to about 75 minutes, preferably about 30 minutes to about 60 minutes) after the bolus dosage was initiated in operation 620. As previously described, the controller device 200 can evaluate whether user's blood glucose levels are decreasing within the predetermined period of time and that the rate of change of the user's blood glucose levels is also decreasing. In alternative embodiments, the controller device 200 can evaluate only whether the rate of change of the user's blood glucose levels is decreasing during the predetermined period of time.

If the determination in operation 630 indicates that the user's blood glucose level is decreasing, that the rate of change of the user's blood glucose level is changing, or both, the method 600 can return to operation 605 (where the time $t_1$ is then reset to the present time). Such a determination would indicate to the controller device 200 of the infusion system that the bolus dosage of medicine was (or is being) properly dispensed to the user's body via the user set 146.

If, however, the determination in operation 630 indicates that the user's blood glucose level is not decreasing, that the rate of change of the user's blood glucose level is not decreasing, or both, the method 600 can continue to operation 635 in which the pump system outputs an alert indicative of a possible problem with the infusion set device. For example, as previously described in connection with FIG. 12B, the alert can be output from the infusion pump system 10 in the form of a textual alert message and, optionally, an audible or vibratory alarm and a temporary illumination of the aforementioned flashlight instrument 230.

The method 600 may also include the operation 640 in which the infusion pump system prompts the user to take one or more corrective actions. For example, the user interface 220 of the infusion pump system can prompt the user to replace the infusion set 146, to review a troubleshooting guide (e.g., displayed on the user interface 220 or on another external device), or a combination thereof. Such a troubleshooting guide may cause the infusion pump system 10 to display to the user a series of questions and instructions for the user to identify possible errors with the infusion pump system 10 or the infusion set 146 that might have caused the previously initiated bolus dosage to be less effective than desired.

As shown in operation 650, if the infusion pump system receives user input indicative of an instruction to silence the alarm (e.g., which was emitted during operation 635, 640, or both), the method can continue to operation 655 so that the alarm (e.g., visual, audible, vibratory, or a combination thereof) is silenced for a predetermined period of time (e.g., about 10 minutes to about 120 minutes hours, about 20 minutes hours to about 60 minutes, and preferably about 30 minutes in this example). For example, as previously described in connection with FIG. 12B, the user can select a button on the user interface 200 to indicate an instruction to the silence the alarm (operation 655 in FIG. 13) before returning to operation 635 (FIG. 13).

If the infusion pump system does not receive user input to silence the alarm in operation 650, the method 600 can continue to operation 660. In operation 660, if the infusion pump system receives user input indicative of an instruction to cancel the alarm (e.g., because the infusion set 146 was replaced or reseated on the user's body), the method 600 can return to operation 605 (where the time $t_1$ is then reset to the present time). For example, as previously described in connection with FIG. 12B, the user can select a button that indicates the user has replaced the infusion set 146 with a newly seated infusion 146 or otherwise verified the infusion set 146 is properly secured at the skin penetration point. Alternatively, in operation 660, if the infusion pump system does not receive user input indicative of an instruction to cancel the alarm, the method 600 can return to operation 635 so that the alert is output again (or continued to be output) via the user interface of the pump system.

Figure 14:
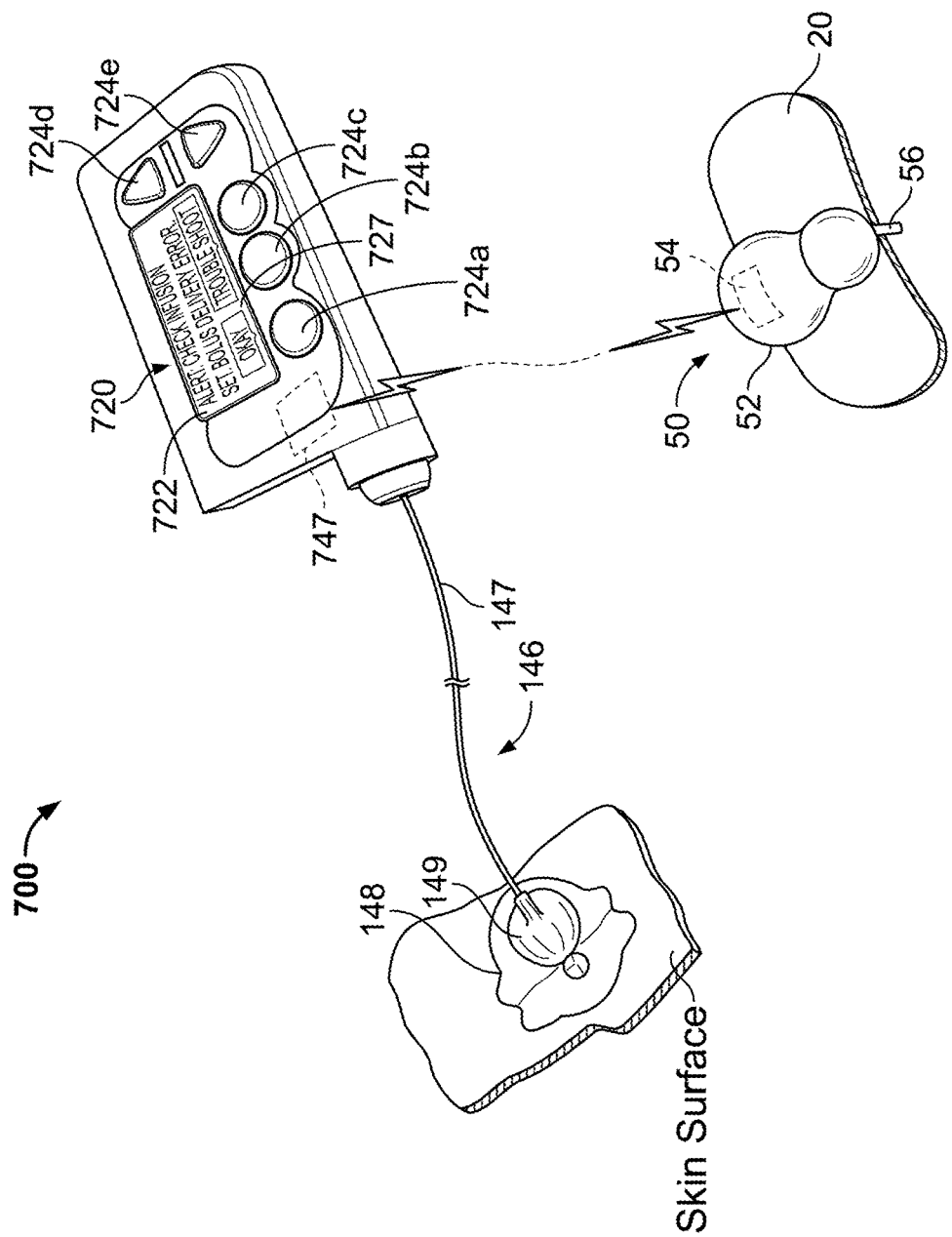
FIG. 14 is a perspective view of an alternative infusion pump system configured to detect a potential problem with an infusion set device, in accordance with some embodiments.

Referring now to FIG. 14, some embodiments of a portable infusion pump system 700 employing one or more of the aforementioned safety features (e.g., similar to those depicted in any of FIGS. 12A-13) can employ a reusable pump apparatus (rather than a disposable pump device as previously described). In such circumstances, the infusion pump system 700 may comprise a reusable device that houses the control circuitry and the pump drive system within a single housing construct. The particular embodiment depicted in FIG. 14 is structurally similar to the pump system depicted in FIG. 11, but may be additionally or alternatively configured to alert the user to a potential problem with an infusion set 146 based at least in part on an analysis of the user's blood glucose levels during a period of time after medicine is dispensed from the infusion pump reservoir. Accordingly, the pump system 700 comprises a reusable pump device that houses both the control circuitry and the pump drive system (which may include a piston rod and one or more gears). Also, the pump system 700 can include a housing structure that defines a cavity in which a medicine cartridge can be received (not shown in FIG. 14; refer for example to cartridge 120 in FIG. 2). For example, the pump system 700 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 700 on the user's skin under clothing or in the user's pocket while receiving the medicine dispensed through the infusion set 146.

The pump system 700 can also communicate with the aforementioned glucose monitoring device 50 for the purpose of receiving data indicative of a user's blood glucose level. Similar to previously described embodiments, the pump system 700 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit. As shown in FIG. 14, the glucose monitoring device 50 can include the housing 52, the wireless communication device 54, and the sensor shaft 56 (similar to the embodiment described in connection with FIG. 1). In response to the measurements made by the sensor shaft 56, the glucose monitoring device 50 can employ the wireless communication device 54 to transmit data to a corresponding wireless communication device 747 housed in the pump system 700. Also, as previously described in connection with FIGS. 12A-13, the user's blood glucose data can be employed by control circuitry housed in the pump system 700 to detect possible problems with the infusion set 146.

For example, after a bolus dosage is initiated from the pump system 700 (e.g., due to user input on the interface 720 requesting a bolus dosage), the infusion pump system 700 can cause the bolus of insulin or other medication to be dispensed from the reservoir and through the infusion set tubing 147. As shown in FIG. 14, the infusion pump system 700 can output an alert indicative of a possible problem with the infusion set 146 in response to a pattern of the user's blood glucose levels over a predetermined period of time (e.g., about 15 minutes to about 75 minutes, preferably about 30 minutes to about 60 minutes in this embodiment) after initial dispensation of a bolus dosage. In this example, the alert is provided to the user in the form of a textual alert message and, optionally, an audible or vibratory alarm.

Similar to the embodiments described in connection with FIG. 13, the alert is output from the pump system 700 in response to the control circuitry (housed in the system 700) determining that user's blood glucose levels are not decreasing within the predetermined period of time, that the rate of change of the user's blood glucose levels is also not decreasing, or both. The infusion pump system 700 can output the alert indicative of a potential problem with the infusion set 146 and may furthermore prompt the user to take one or more corrective actions. For example, the user interface 220 of the infusion pump system can prompt the user to replace the infusion set 146, to review a troubleshooting guide (e.g., displayed on the user interface 220 or on another external device), or a combination thereof. For example, the user can select a button 724a that indicates the user has replaced the infusion set 146 with a newly seated infusion 146 or otherwise verified the infusion set 146 is properly secured at the skin penetration point. Alternatively, the user can select a button 224c that indicates the user is requesting troubleshooting instructions, which then display to the user a series of questions and instructions for the user to identify possible errors with the infusion pump system 700 or the infusion set 146 that might have caused the previously initiated bolus dosage to be less effective than desired. In addition, the pump system 700 can be configured to provide an onscreen option so that the user can select a different button indicating that the user wishes to the silence the alert, which will then silence the alert (either permanently or for a predetermined period of time, such as about 10 minutes to about 120 minutes hours, about 20 minutes hours to about 60 minutes, and preferably about 30 minutes in this example).

Figure 15:
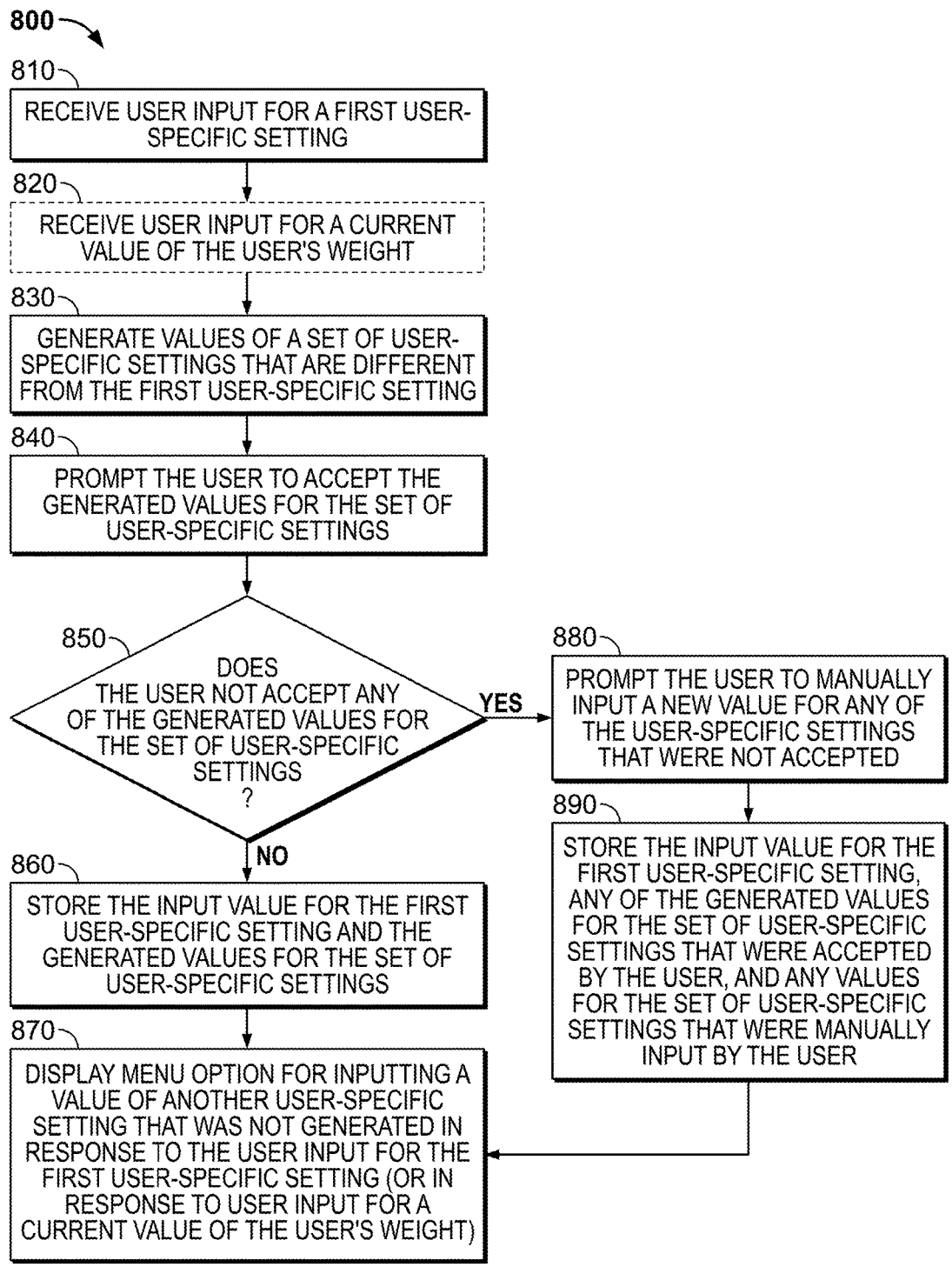
FIG. 15 is a process chart describing a method of controlling an infusion pump system, in accordance with some embodiments.

Referring now to FIG. 15, some embodiments of an infusion pump system (such as the system 10 depicted in FIGS. 1-8B and 12A-B or the system 500 or 700 depicted in FIGS. 11 and 14) can be configured to automatically populate suitable values for a plurality of user-specific settings in response to user input related to one or two other user-specific settings. For example, during an initial setup process for the pump system 10, 500, or 700, the pump system can prompt the user via the user interface to input a value for the a total daily dosage (and optionally, a value for the user's current weight), which would then cause the pump system to calculate (and automatically populate) suitable values for a set of various other user-specific settings (e.g., basal rate, maximum daily basal dosage, maximum daily bolus dosage, insulin sensitivity, carb ratio, and the like). In doing so, the pump system can be configured to display the automatically generated values for review by the user, and to furthermore prompt the user to accept the automatically generated values for the user-specific settings. If the user does not accept one or more of the automatically generated values for the user-specific settings, the user interface can direct the user to the menu screen that prompts the user to manually input a new value for the particular user-specific setting.

In some implementations, the infusion pump system can perform a method 800 for controlling an infusion pump system so as to automatically calculate values for a plurality of user-specific settings in response to user input related to one or more different user-specific settings. As shown in the non-limiting example depicted in FIG. 15, the method 800 can include an operation 810 of receiving user input indicative of a new value for a first user-specific setting. This information can be prompted by the user interface of the pump system, for example, in the form of a query presented on the display device. In the example described below, the first user-specific setting can be the user's total daily dosage based on the user's previous history of insulin injections (e.g., prior to using an infusion pump system). Alternatively, the first user-specific setting can be the user's total daily dosage based on the user's previous history of pump usage (e.g., total daily dosage based on usage of a different pump system). Also, in another alternative, the first user-specific setting can be the user's total daily basal dosage based on the user's previous history of pump usage.

Optionally, the method 800 may also include operation 820 in which the pump system receives user input indicative of a value for the user's weight. Again, this information can be prompted by the user interface of the pump system, for example, in the form of a query presented on the display device.

In operation 830, the infusion pump system can be configured to generate values for a set of user-specific settings (which are different from the first user-specific setting) in response to the user input of the value for the first user-specific setting (or, optionally, in response to input values for both the first user-specific setting and the user's weight). In this example, if the newly input value for the first user-specific setting is the user's total daily dosage based on the user's previous history of insulin injections (e.g., prior to using an infusion pump system), the pump system can be configured to automatically calculate values for a set of user-specific settings such as the basal rate, maximum daily basal dosage, maximum daily bolus dosage, insulin sensitivity, carb ratio, and others.

For example, the user's total daily dosage based on the user's previous history of insulin injections ($TDD_{injections}$) can be used to automatically calculate some of these values as follows:

Basal Rate=[$TDD_{injections}$]/60, where Basal Rate is in Units/hour (alternatively, where the input the user's total daily dosage based on the user's previous usage of an insulin pump system ($TDD_{insulin\ pump\ history}$), then Basal Rate=[$TDD_{insulin\ pump\ history}$]/50);

Maximum Basal Rate=[$TDD_{injections}$]×(1.2), where Maximum Basal Rate is in Units of Insulin per hour;

Maximum Bolus Dosage=[$TDD_{injections}$]×(0.25), where Maximum Bolus Dosage is in Units of Insulin;

Insulin Sensitivity=(2450)/[$TDD_{injections}$], where Insulin Sensitivity is in units of mg/dl/Unit; and Carb Ratio=[3.25*(Weight)]/[$TDD_{injections}$], where Carb Ratio is in units of grams/Unit, and the user's weight in lbs (alternatively, where the user's weight is unknown, then Carb Ratio=[450/[$TDD_{injections}$]]).

It should be understood from the description herein, that the Basal Rate parameter would be applied in the pump system as a uniform basal rate across a 24-hour period (e.g., a flat profile). Alternatively, the pump system can be configured to automatically apply the Basal Rate parameter so that the amount of daily basal dosage is output according to a preset basal profile pattern. In such circumstances, the basal dosages are not applied in a flat profile across a 24-hour period, but instead the basal rate amounts may be slightly greater than the Basal Rate parameter (as calculated above) during some schedule periods in each day and may be slightly less than the Basal Rate parameter (as calculated above) during other schedule periods in each day. For example, the predefined basal profile can be automatically selected by the pump system so that the basal delivery rates account for treating dawn phenomenon (e.g., an increase in the basal rate in the early morning hours) or avoiding low glucose levels in the nighttime (e.g., a decrease in the basal rate from about 9:00 pm until the early morning hours). Such basal patterns may be automatically implemented by the pump system, or alternative, can be selectable by the user via user interface. For example, after operation 810 (described above), the user interface of the pump system can prompt the user to select one or both options of "treat dawn phenomenon" and "avoid overnight lows."

Furthermore, in an alternative example, the user's average hourly basal rate (based on the user's previous usage of an insulin pump system), rather than the user's total daily dosage, can be input to automatically calculate some of the aforementioned values. For instance, the user can input a basal rate, and the pump system can be configured automatically calculate values for the Total Daily Dosage, Maximum Basal Rate, Maximum Bolus Dosage, Insulin Sensitivity, and the Carb Ratio.

Still referring to FIG. 15, the method 800 may also include operation 840 in which the pump system prompts the user to accept the generated values for the set of user-specific settings. For example, the user interface of the pump system can display the calculated values for each of the user-specific settings (e.g., either presented in serial screens, or in a "summary" listing), and the user interface can query the user to "accept" or "modify" any of the calculated values.

If the user provides input indicative of acceptance of all of the generated values for the set of user-specific settings, the method 800 can continue to operation 860 in which the pump system stores the input value for the first user-specific setting and the generated values for the set of user-specific settings. As previously described, the pump system can be equipped with one or more computer-readable memory devices that are in communication with the internal control circuitry, and the input value for the first user-specific setting and the generated values for the set of user-specific settings can be stored in one or more of these memory devices.

After these values are stored, the method 800 can continue to operation 870 in which the pump system prompts the user for additional information related to other user-specific settings that were not generated in response to the user input for the first user-specific setting. For example, the pump system can provide a menu option on a display device of the user interface that prompts the user to input a value for another user-specific setting that was not generated in response to the user input for the first user-specific setting.

Referring again to operation 850 (described above), if the user provides input indicating a non-acceptance of one or more of the generated values for the set of user-specific settings, the method 800 can continue to operation 880 in which the pump system prompts the user to manually input a new value for any of the user-specific settings that were not accepted. For example, the pump system can provide a menu option on the display device of the user interface that prompts the user to manually input a new value for the particular user-specific setting that was not accepted by the user.

From there, the method 800 may optionally continue to operation 890 in which the pump system stores the various values that were initially input, automatically generated, or manually input after the automatic generation of values. In particular, the pump system can be configured to store the input value for the first user-specific setting, any of the generated values for the set of user-specific settings that were accepted by the user, and any values for the set of user-specific settings that were manually input by the user (e.g., replacing the non-accepted, automatically generated value). After these values are stored, the method 800 can continue to operation 870 in which the pump system prompts the user for additional information related to other user-specific settings that were not generated in response to the user input for the first user-specific setting (as previously described above).

A number of embodiments of the invention have been described. Nevertheless, it will be understood that various modifications may be made without departing from the spirit and scope of the invention. Accordingly, other embodiments are within the scope of the following claims.

What is claimed is:

1. A method of operating a portable insulin infusion system, the method comprising:
   receiving manual user input at a user interface of the insulin infusion system indicative of a value for a first user-specific setting for a first parameter type, the first parameter type being a user's insulin sensitivity or a user's carbohydrate ratio;
   retrieving a previously stored value for a second user-specific setting for a second parameter type, the second parameter type being a total daily basal dosage amount for the user;
   determining, using the value for the second user-specific setting, a range for the first parameter type, wherein a first upper threshold for the range and a first lower threshold for the range is determined as a function of the total daily basal dosage amount for the user, the first upper threshold being different than the first lower threshold;
   comparing the value for the first user-specific setting to the determined range for the first parameter type to determine that the value for the first user-specific setting is outside of the range for the first parameter type;
   receiving data indicative of the user's blood glucose level from a glucose monitoring device;
   calculating a recommended bolus amount based at least in part on the first parameter type;
   displaying the recommended bolus amount to the user on a user interface of the insulin infusion system; and
   outputting an alert in response to determining that the value for the first user-specific setting is outside of the range for the first parameter type.

2. The method of claim 1, wherein the alert comprises a textual alert message indicating that an input value for the first user-specific setting is out of balance with the previously stored value for the second user-specific setting.

3. The method of claim 1, further comprising, in response to determining that the value for the first user-specific setting is outside of the range for the first parameter type, prompting the user to select a first option via a user interface indicative of an instruction to continue with the value for the first user-specific setting or to select a second option via the user interface indicative of an instruction to provide a new value for the first user-specific setting, wherein the first option and second option are contemporaneously displayed via the user interface.

4. The method of claim 3, wherein in response to user selection of the first option via the user interface, the user input for the first user-specific setting is stored in a memory device.

5. The method of claim 3, wherein in response to user selection of the second option via the user interface, prompting the user to input the new value for the first user-specific setting via the user interface.

6. The method of claim 1 wherein the first parameter type is the user's insulin sensitivity.

7. The method of claim 6, wherein the recommended bolus is a correction bolus that is determined using the user's blood glucose level and the user's insulin sensitivity.

8. The method of claim 1, wherein the insulin infusion system comprises a disposable and non-reusable insulin delivery device and a removable controller device,
the insulin delivery device comprising:
an insulin cartridge comprising a plunger, a septum, and insulin
a housing that retains the insulin cartridge; and
a drive system comprising a piston rod that is incrementally movable to apply a dispensing force to the plunger to dispense insulin through the septum;
the removable controller comprising:
a controller housing that is removably attachable to the housing of the insulin delivery device; and
a wireless communication device to receive the user's blood glucose level from the glucose monitoring device.

9. A method of operating a portable insulin infusion pump system, the method comprising:
dispensing insulin from a portable housing of an infusion pump system; and
storing a total daily basal dosage amount for a user;
calculating an insulin sensitivity range using the stored total daily basal dosage amount for the user, the insulin sensitivity range having a first upper threshold that is distinct from a first lower threshold of the insulin sensitivity range;
determining that a stored insulin sensitivity value for the user is outside of the calculated insulin sensitivity range; and
outputting an alert via a user interface of the system in response to determining that the stored insulin sensitivity value for the user is outside of the calculated insulin sensitivity range.

10. The method of claim 9, wherein the alert comprises a textual alert message indicating that the stored insulin sensitivity value for the user is out of balance with the stored total daily basal dosage amount for the user.

11. The method of claim 9, further comprising, in response to determining that a stored insulin sensitivity value for the user is outside of the calculated insulin sensitivity range, prompting the user to select a first option via a user interface indicative of an instruction to continue operating with the stored insulin sensitivity value for the user or to select a second option via the user interface indicative of an instruction to provide a new value for the insulin sensitivity value for the user, wherein the first option and second option are contemporaneously displayed via the user interface.

12. The method of claim 11, wherein in response to user selection of the second option via the user interface, prompting the user to input the new value for the insulin sensitivity value for the user via the user interface.

13. A method of operating a portable infusion pump system comprising:
dispensing medicine from a portable housing of an infusion pump system;
receiving user input at a user interface of the infusion pump system to initiate a first bolus dosage of the medicine;
receiving, at the infusion pump system and after receiving the user input to initiate the first bolus dosage, blood glucose information indicative of a user's blood glucose measurements over a period of time, the blood glucose information being obtained from a blood glucose meter device and/or a glucose monitoring device;
determining a rate of change of the user's blood glucose measurements over the period of time;
identifying that an infusion set error of a second bolus dosage administered prior to receiving the user input to initiate the first bolus dosage has occurred based on determining that the rate of change of the user's blood glucose measurements has not decreased over the predetermined period of time; and
outputting an alert via the user interface of the infusion pump system in response to the infusion pump system identifying that the infusion set error has occurred based on determining that the rate of change of the user's blood glucose measurements has not decreased over the predetermined period of time.

14. The method of claim 13, wherein the alert output via the user interface comprises a textual alert message indicating the infusion set error.

15. The method of claim 13, and wherein the infusion pump system detects the infusion set error in response to a determination by the infusion pump system that the blood glucose information indicates that a user's blood glucose level is not decreasing over a predetermined period of time after initiating the first bolus dosage.

* * * * *